(12) United States Patent
Jia et al.

(10) Patent No.: US 9,549,683 B2
(45) Date of Patent: *Jan. 24, 2017

(54) SENSING ZONE FOR SPATIALLY RELEVANT ELECTRICAL INFORMATION

(71) Applicant: CARDIOINSIGHT TECHNOLOGIES, INC., Cleveland, OH (US)

(72) Inventors: Ping Jia, Solon, OH (US); Charulatha Ramanathan, Solon, OH (US); Maria Strom, Mayfield Heights, OH (US); Brian P. George, Medina, OH (US); Lalita Bhetwal, Mentor, OH (US); Harold Wodlinger, Thornhill (CA); Jonathan D. Small, Avon, OH (US)

(73) Assignee: Cardioinsight Technologies, Inc., Cleveland, OH (US)

( * ) Notice: Subject to any disclaimer, the term of this patent is extended or adjusted under 35 U.S.C. 154(b) by 273 days.

This patent is subject to a terminal disclaimer.

(21) Appl. No.: 13/650,678

(22) Filed: Oct. 12, 2012

(65) Prior Publication Data

US 2013/0131529 A1    May 23, 2013

Related U.S. Application Data

(60) Provisional application No. 61/546,083, filed on Oct. 12, 2011.

(51) Int. Cl.
*A61N 1/368*    (2006.01)
*A61N 1/365*    (2006.01)
(Continued)

(52) U.S. Cl.
CPC ........... *A61B 5/044* (2013.01); *A61B 5/04012* (2013.01); *A61B 5/0432* (2013.01); *A61B 5/0452* (2013.01)

(58) Field of Classification Search
CPC .............................. A61B 5/0432; A61B 5/044
(Continued)

(56) References Cited

U.S. PATENT DOCUMENTS 5,483,968 A * 1/1996 Adam et al. ................... 600/508
8,838,203 B2 * 9/2014 van Dam et al. ............. 600/411
(Continued)

FOREIGN PATENT DOCUMENTS

EP    2266459 A1    12/2010
JP    62217936 A    9/1987
(Continued)

OTHER PUBLICATIONS

Int'l Search Report—3pgs., Mar. 25, 2013, CardioInsight Technologies, Inc.

(Continued)

*Primary Examiner* — Christopher D Koharski
*Assistant Examiner* — Jeremiah Kimball
(74) *Attorney, Agent, or Firm* — Tarolli, Sundheim, Covell & Tummino LLP

(57) ABSTRACT

Systems and methods are disclosed to determine one or more sensing zones on a body surface for electrocardiographic mapping of a region of interest associated with the heart. The sensing zone can be utilized to facilitate acquisition, processing and mapping of electrical activity for the corresponding region of interest. In other examples, an application-specific arrangement of electrodes can also be provided based on the sensing zone that is determined for the region of interest.

32 Claims, 12 Drawing Sheets

(51) Int. Cl.
*A61B 5/044* (2006.01)
*A61B 5/04* (2006.01)
*A61B 5/0432* (2006.01)
*A61B 5/0452* (2006.01)

(58) Field of Classification Search
USPC ............... 600/509, 523, 382, 388, 380, 393
See application file for complete search history.

(56) References Cited

U.S. PATENT DOCUMENTS

| | | | |
|---|---|---|---|
| 9,186,515 B2* | 11/2015 | Ramanathan | G06F 19/3481 |
| 2002/0128565 A1* | 9/2002 | Rudy | 600/509 |
| 2003/0120163 A1* | 6/2003 | Rudy et al. | 600/509 |
| 2004/0082870 A1* | 4/2004 | Rudy et al. | 600/509 |
| 2007/0073179 A1 | 3/2007 | Afonso et al. | |
| 2008/0058657 A1 | 3/2008 | Schwartz et al. | |
| 2008/0154110 A1* | 6/2008 | Burnes et al. | 600/382 |
| 2009/0053102 A2 | 2/2009 | Rudy et al. | 422/24 |
| 2009/0069704 A1 | 3/2009 | MacAdam | |
| 2010/0191131 A1* | 7/2010 | Revishvili et al. | 600/509 |
| 2011/0190649 A1* | 8/2011 | Rudy | A61B 5/04085 600/509 |
| 2011/0206256 A1* | 8/2011 | Ramanathan | A61B 5/04021 382/128 |
| 2014/0135866 A1* | 5/2014 | Ramanathan et al. | 607/18 |
| 2016/0067489 A1* | 3/2016 | Ramanathan | G06F 19/3481 607/17 |

FOREIGN PATENT DOCUMENTS

| | | |
|---|---|---|
| JP | 6125883 A | 5/1994 |
| JP | 2001-070269 A | 3/2001 |
| JP | 2005323821 A | 11/2005 |
| JP | 2007-061617 A | 3/2007 |
| JP | 2007-268034 A | 10/2007 |
| JP | 2008068084 A | 3/2008 |
| JP | 2009-537252 A | 10/2009 |
| JP | 2011530388 A | 12/2011 |
| JP | 2012508079 A5 | 12/2012 |
| JP | 05197767 B2 | 5/2013 |
| WO | 2010019494 A1 | 2/2010 |
| WO | 2010054320 A1 | 5/2010 |
| WO | 2010054409 A1 | 5/2010 |
| WO | WO 2010054352 A1 * | 5/2010 ............ A61B 5/04 |

OTHER PUBLICATIONS

Written Opinion—4 pgs., Mar. 25, 2013, CardioInsight Technologies, Inc.
Int'l Preliminary Report—5pgs., Apr. 15, 2014, CardioInsight Technologies, Inc.
Supplementary European Search Report dated Jun. 9, 2015.
Japanese Patent Application No. 2014-535919; Office Action Mailing (English Translation) Date: Jun. 2, 2015; pp. 1-5.

* cited by examiner

SENSING ZONE FOR SPATIALLY RELEVANT ELECTRICAL INFORMATION

CROSS-REFERENCE TO RELATED APPLICATION

This application claims the benefit of U.S. Provisional Patent Application No. 61/546,083, filed Oct. 12, 2011, and entitled METHOD AND SYSTEM TO DETERMINE A SENSING ZONE TO FACILITATE ELECTROCARDIOGRAPHIC MAPPING AND ELECTRODE ARRANGEMENT FOR ECM, the entire contents of which is incorporated herein by reference.

TECHNICAL FIELD

This disclosure relates to a sensing zone that can be used to obtaining spatially relevant electrical information, such as for one or more regions of an anatomical structure.

BACKGROUND

Body surface mapping (BSM) is well known art in electrocardiography. BSM involves recording electrocardiograms from several locations on the body surface. The principle of body surface mapping is to obtain the heart's electrical activity in a spatially comprehensive manner as possible.

Electrocardiographic mapping (ECM) is a technology that is used to determine heart electrical data from non-invasively measured body surface electrical signals, such as measured from BSM or other non-invasive electrical sensors. The resulting heart electrical data can be utilized to generate an output, such as a graphical map of heart electrical activity.

SUMMARY

This disclosure relates to a sensing zone that can be used to obtaining spatially relevant electrical information, such as for one or more regions of an anatomical structure. The sensing zone can provide very sensitive and specific data pertaining to the electrical activity of the heart, globally and regionally. This has several applications, including to facilitate electrocardiographic mapping (ECM) and analysis.

For example, one or more sensing zones can be determined for a selected region of interest. Electrical activity thus can be sensed for the sensing zone, such as by using an application-specific arrangement of electrodes. The electrical activity for a given predetermined sensing zone on the body surface can provide a surrogate estimate for electrical activity of the region of interest, which be displayed in a graphical map for the region of interest. In other examples, the electrical activity for the sensing zone can be mapped via electrocardiographic mapping on to a cardiac envelope such as to display reconstructed electrical activity for the region of interest.

As one example, a computer-implemented method can include identifying a region of interest for an anatomical structure located within a patient's body. A zone on a body surface of the patient can be determined, based on analysis of electrical activity for the region of interest relative to electrical activity on the body surface, such that electrical activity for the zone on the body surface provides a surrogate estimate for electrical activity of the region of interest.

As another example, a non-transitory computer-readable medium having instructions stored thereon, the instructions being executable by a processor to perform a method. The method can include accessing electrical data measured from at least a predetermined sensing zone on a body surface of a patient that is spaced apart from a given region of interest of the heart. A surrogate estimate for electrical activity of the given region of interest can be determined based on the electrical data for the predetermined sensing zone on the body surface.

As another example, a non-transitory computer-readable medium having instructions stored thereon, the instructions being executable by a processor to perform a method. The method can include accessing electrical data measured from at least a predetermined sensing zone on a body surface of a patient that is spaced apart from a given region of interest of the heart. Electrical activity for the given region of interest of the heart can be determined based on geometry data and the electrical data for the predetermined sensing zone on the body surface. A graphical map of electrical activity can be generated for the given region of interest of the heart based on the reconstructed electrical activity.

As yet another example, a non-transitory computer-readable medium having instructions executable by a processor. The instructions can include a channel detector to determine at least one input channel expected to affect mapping of body surface electrical activity within a sensing zone that comprises a proper subset of available input channels. A resolution calculator can compute coefficients of a transformation matrix for each of the at least one input channel in the sensing zone. An evaluator can identify a low resolution anatomical spatial region based on an evaluation of the coefficients.

DETAILED DESCRIPTION

Figure 1:
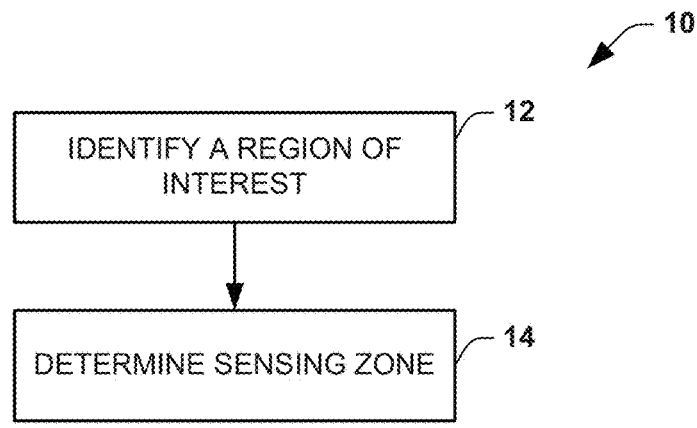
FIG. 1 is a flow diagram that illustrates an example of a method to determine a sensing zone for a region of interest.

This disclosure provides systems and methods for determining one or more sensing zones that can be utilized to facilitate evaluating cardiac function. In some examples electrocardiographic mapping (ECM). Also disclosed is an approach to provide a design of electrode arrangements that can be used to acquire data for ECM, such as can be an application-specific arrangement of electrodes.

In some examples, systems and methods disclosed herein can compute a transfer matrix $A^{-1}$ having coefficients that relates heart electrical potentials $V_H$ and body surface potentials $V_B$, such as follows $V_H = A^{-1} \times V_B$. By using this matrix $A^{-1}$, a proper subset of body surface channels and a relevant contributions to each and every node on the heart can be identified. That is, for each node on a cardiac envelope, the matrix $A^{-1}$ can identify a set of electrode locations, which defines a zone, having a greatest contribution to the respective node. For a given region of interest (ROI) of the heart, which can include one or more nodes, a corresponding the matrix $A^{-1}$ can be computed to identify a set of electrode locations (a zone) having the greatest contribution to the nodes that define the ROI. As used herein, the terms "region" and "ROI" as applied to a given surface of an anatomical structure or envelope means something less than the entire surface. For example, some well known regions of the heart include the right-ventricular (RV) freewall region, the anterior left ventricular (LV) region, the lateral left ventricular region, the apex, the left ventricular base and the like.

The set of body surface channels contributing the greatest amount for a given ROI form a group of channels that are referred to herein as a sensing zone. As one example, the sensing zone can correspond to a critical set of electrodes necessary and sufficient to generate an accurate ECM.

As another example, electrical activity for a predetermined sensing zone on the body surface provides a surrogate estimate for electrical activity of the region of interest. Thus, electrical activity measured from a given sensing zone can be utilized to understand and characterize electrical activity of the corresponding ROI. Moreover electrical activity measured for a plurality of different sensing zones can be analyzed to provide spatially and temporally consistent electrical information for multiple ROIs of the heart and even across the entire heart. For instance, the analysis can include computing electrical function characteristics, such as activation time, repolarization time, synchrony and the like, from the measured body surface electrical signals for each respective sensing zone. The computed electrical characteristics can be analyzed to understand relative cardiac electrical function among different ROIs of the heart, for example, by providing a graphical map of the measured body surface electrical signals, such as a potential map, or a map of the computed electrical characteristics.

The sensing zone can vary depending on an ROI that is selected and/or application for which the ECM is being generated. For example, in some applications (e.g., cardiac resynchronization therapy (CRT)), a greater level of accuracy may be desired such that the sensing zone can be determined to include a number of electrode sensing locations sufficient to afford the desired accuracy. In other situations, an even greater reduced subset of electrode sensing locations may be adequate. The sensing zone can include a contiguous set of body surface electrode sensing locations. Additionally or alternatively, the sensing zone can include non-contiguous clusters of one or more body surface electrode sensing locations. The distribution and arrangement of electrode sensing locations for a given sensing zone can vary depending on the selected ROI. The ROI can range, for example, from a single node of a cardiac envelope to the entire heart.

As a further example, the set of body surface electrode sensing locations corresponding to the sensing zone can provide a reduced set of electrodes necessary and sufficient for ECM computations for each given ROI. As a result, application specific or special purpose vests and arrangements of sensing electrodes can be provided for use in ECM, such as one or more electrode arrangements configured with electrodes in different sensing zones for corresponding different applications. For example, a simplified sensing vest with an arrangement of electrodes can be provided for one or more ROIs on the heart, such as one or more ventricles. Such special purpose arrangement of sensing electrodes can have fewer electrodes than a general purpose vest that can include electrodes covering the entire torso in an evenly distributed arrangement. Additionally or alternatively, an arrangement of electrodes can be provided for a predetermined sensing zone configured for reconstructing heart electrical activity for one or more atria of a patient. Similar specially designed vests can also be configured for other ROIs of different anatomical or geometrical structures.

As a further example, by knowing the sensing zone for a selected ROI, systems and methods disclosed herein can readily determine if a bad channel exists outside of the sensing zone it will have little if any impact on ECM results. Thus, there may be no need to correct for such a bad channel. In contrast, if a bad channel or electrode is determined to exist within a desired sensing zone, an appropriate warning can be generated to prompt the user to take corrective action. The impact of one or more bad channels on the resulting resolution of maps that can be generated from the measured body surface electrical activity can also be ascertained. For example, one or more low resolution regions on the heart can be determined and displayed in a corresponding graphical map.

Additionally, by understanding the body surface electrode locations corresponding to the sensing zone, systems and methods disclosed herein can be programmed to provide guidance to facilitate application of other sensing and therapy devices (e.g., defibrillator patches, guidance electrodes and the like) to locations that reside outside of a sensing zone or minimize overlap with a sensing zone, as appropriate. Additionally, if a sensing zone is known for a given application, a reduced set of sensing data can be acquired (since there are fewer channels) to facilitate the resulting computations in translating the body surface electrical signals to corresponding reconstructed cardiac electrical signals on a cardiac envelope. Such computations thus can employ a set of contributing transfer matrix coefficients determined according to the electrode sensing locations. In other examples, the measured electrical activity for the sensing zone (or other electrical characteristics computed therefrom) can be utilized as a surrogate estimate of electrical activity for the corresponding ROI on the heart.

FIG. 1 is a flow diagram 10 demonstrating an example method for determining a sensing zone corresponding to a given ROI. The method can include a computer implemented-method that employs instructions, executable by a processor, such as can be stored in a non-transitory machine readable medium (e.g., volatile or non-volatile memory). The method can also involve the use of electrodes for sensing electrical activity, which can be positioned on a patient for measuring electrical activity for one or more sensing zone.

In FIG. 1, the method 10 includes identifying a ROI, at 12. The ROI can be identified in response to a user input such as entered via a user input device (e.g., mouse, keyboard, touchscreen) of a computer implementing the method. For instance, the user input can include access functions to select one or more ROI of the heart, to acquire body surface electrical data, to initiate a mapping function or the like. As disclosed herein, the ROI can correspond to an anatomic region or surface area of an anatomical structure within the patient's body, such as patient's heart or some other geometric construct (e.g., a cardiac envelope). For instance, an ROI can include the ventricles or atria or other region of interest, which may vary according to application requirements.

In the example of FIG. 1, after the ROI has been ascertained, a corresponding sensing zone can be determined at 14. The sensing zone can be determined at 14 to encompass one or more body surface locations on which electrodes are positioned sufficient to ensure accurate inverse reconstruction of the body surface electrical measurements to corresponding cardiac electrical activity for the identified ROI. The determination can be made based on understanding the relative contribution of each of a plurality of body surface electrodes to nodes within the region of interest. The relative contribution of body surface electrodes to the location within the identified region of interest thus can be utilized to identify the sensing zone via a corresponding transfer matrix $A^{-1}$. The sensing zone for a selected ROI can be determined from data from one patient.

In some examples, the ROI can be further localized by using techniques. For example, such localization techniques can include, in response to applying a therapy (e.g., electrical stimulation pulse) to a known anatomical region and correlating the mapped body surface electrical measurements, an earliest activation signal and/or time can be computed to identify a corresponding sensing zone for the corresponding ROI at which the stimulation was applied.

It is to be understood and appreciated that the actions illustrated in FIG. 1, in other embodiments, may occur in different orders than shown. For example, the region of interest can be identified at 12 based on the zone that has been determined at 14. This can be implemented to identify an ROI of a resultant map (e.g., corresponding to a low resolution region) that may be adversely affected by bad channels determined to reside in the zone. For instance, a bad channel can result from a missing electrode, an inadequate attachment of an electrode on the body surface, low signal-to-noise ratio, manually identifying a channel as bad or missing or combinations of these or other factors. As disclosed herein, one or more such low resolution area can be identified by evaluating coefficients calculated for the channels corresponding to electrodes that reside in the zone. The specificity and/or sensitivity of such evaluation may be fixed or it can be user programmable.

Once the sensing zone has been adequately determined, a simplified arrangement of electrodes can be utilized for analysis. For example, the simplified arrangement of electrodes can be utilized for generating one or more graphical maps based on electrical activity sensed by the arrangement of electrodes, such as demonstrated in FIG. 2. In some examples, the sensed electrical activity can be analyzed to compute ECM. In other examples, the sensed electrical activity can be analyzed to generate body surface maps for the sensing zone, which provides a surrogate estimate for the corresponding ROI of the heart.

Figure 2:
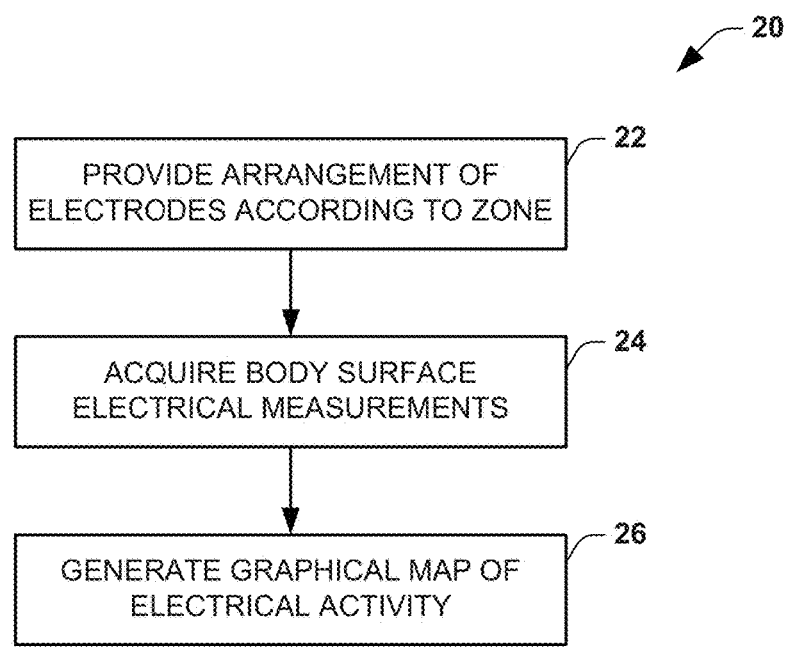
FIG. 2 is a flow diagram illustrating an example of a method of performing electrocardiographic mapping.

In the example of FIG. 2, the method 20 includes providing an arrangement of electrodes according to the determined sensing zone, demonstrated at 22. The arrangement of electrodes can be configured as part of a simplified or custom vest design in which the arrangement of electrodes corresponds to a distribution of electrodes within the sensing zone. In other examples, the sensing zone can correspond to a proper subset of electrodes selected from an array of electrodes, such as may be integrated into a sensing vest or similar construct. If the sensing zone can be known a priori, such as to provide an application-specific arrangement of electrodes, a corresponding transfer matrix $A^{-1}$ can be utilized to translate the body surface electrical signals to a corresponding ROI.

Once the arrangement of electrodes has been positioned on the patient's body surface, including for a given sensing zone, body surface electrical measurements can be acquired at 24. Since the arrangement of electrodes for the given sensing zone is less than a full complement of body surface electrodes surrounding a patient's entire torso, as is done for traditional ECM, the amount of data acquired for ECM can be reduced as to facilitate subsequent processing for visualization.

At 26, a graphical map can be generated for the ROI based on the acquired body surface electrical measurements for the sensing zone. By way of example, a map of body surface electrical activity for the sensing zone can be generated to provide a surrogate estimate for electrical activity of the corresponding ROI. For instance the surface map can be a potential map for the given zone or a plurality of different zones on the body surface where measurements are made via the electrode arrangement (at 22). Alternatively or additionally, the map can include a characterization of electrical activity that is computed from the body surface electrical measurements for the zone. As yet another example, the map can include a characterization of electrical activity that is computed from the body surface electrical measurements for a plurality of different zones, such as to provide a surrogate estimate of corresponding electrical characteristics for a plurality of respective ROIs. The electrical characteristics can include body surface activation times, relative synchrony for the body surface signals, a repolarization or depolarization time calculated from the body surface signals. These and other characteristics for the body surface can provide surrogate estimates for the respective ROIs without requiring imaging or solving the inverse solution.

As another example, the graphical map can be generated based on reconstructed electrical signals corresponding to heart electrical activity. As disclosed herein the reconstructed electrical signals can be generated based on transformation matrix designed for the solving the inverse problem for the body surface electrical measurements for the sensing zone (or set of plural zones) and for reconstruction at each ROI (e.g., on the heart). The map thus can display reconstructed potentials in a potential map for the ROI over one or more time intervals. The maps can also include, for example, activation maps, repolarization maps, dominant frequency maps or maps of other electrical characteristics computed for the ROI based the reconstructed electrical activity.

As mentioned above, since the number electrodes for the sensing zone can be significantly reduced relative to the traditional ECM vest, other objects (e.g., patches, electrodes, or the like) can be positioned on a patient's chest concurrently with the sensing electrodes during the acquisition of body surface measurements (at 24). If such other objects are placed outside of the sensing zones, such objects would not affect the accuracy of the results. Additionally, if such objects were placed within a sensing zone, an appropriate indication or warning could be provided to the user about the adversely affected electrodes. In this way, the user is afforded an opportunity to take corrective action as may be appropriate.

By way of example, if defibrillator patches are required to be applied to a patient's body in particular locations and if a region of interest or regions can be identified in advance, the systems and methods shown and described herein can ascertain which electrodes are part of the sensing zone (or zones) such that if body surface electrodes are removed from the patient's body in order to position the defibrillator patches, the effect can be determined depending on whether or not the removed electrodes were in the sensing zone. For instance, information can be computed and provided to the user (e.g., a graphical map) demonstrating areas affected that may experience a decrease in resolution for one or more ROI. Thus, guidance can be provided to facilitate placements of such defibrillator patches or other objects depending upon the region of interest. In some cases, the region of low resolution may reside outside a ROI that is being evaluated such that it can be ignored. In other examples, the low resolution area may be within or overlap with the ROI such that corrective action (e.g., re-location of electrodes) may be needed before analysis of electrical activity for the ROI.

Additionally or alternatively, as mentioned, specific vest designs can be created for particular applications such as may provide openings or access to the body surface to facilitate placements of defibrillator patches or other objects on the patient's torso while retaining the set of electrodes in the sensing zone.

Figure 3:
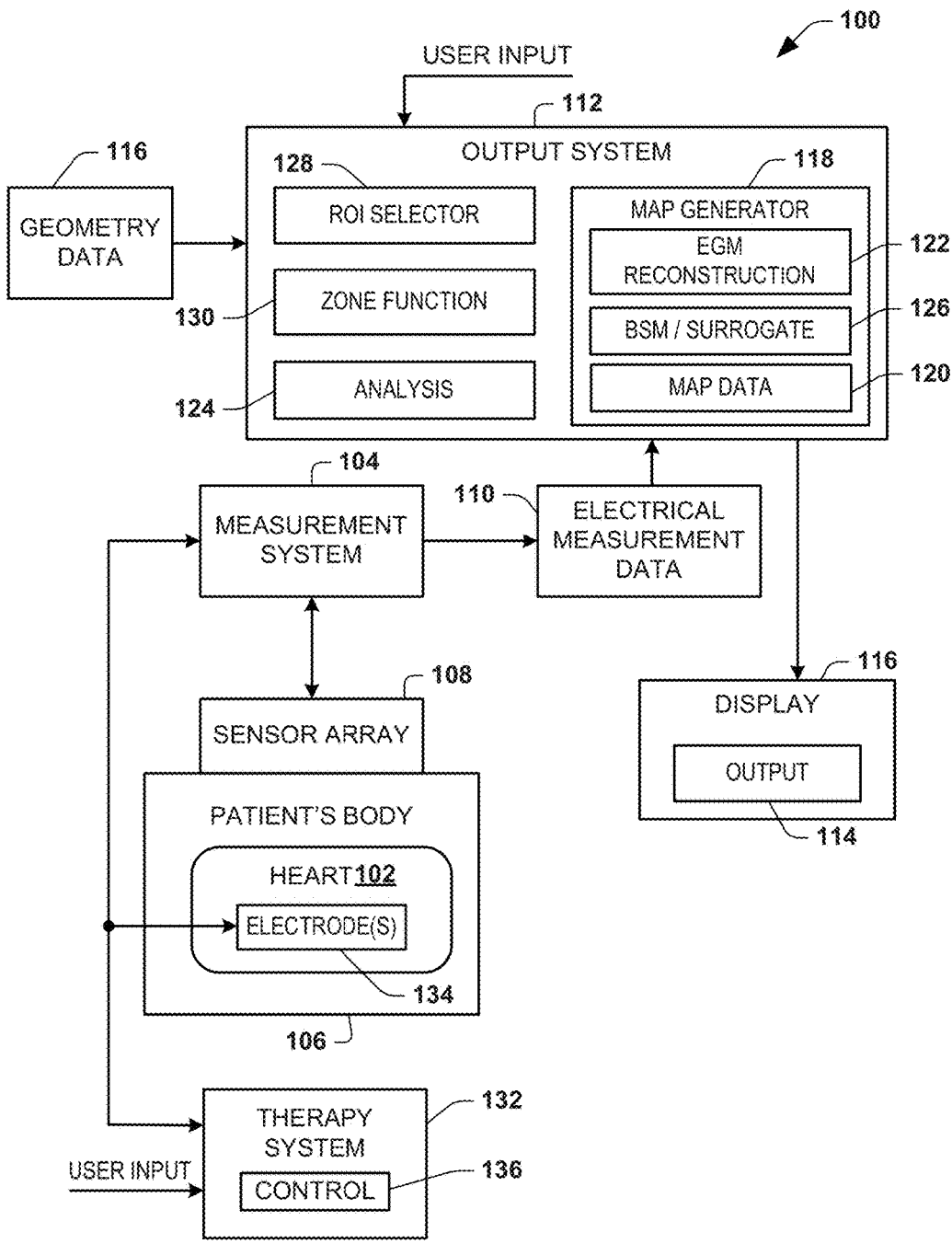
FIG. 3 depicts an example of a system to perform electrocardiographic mapping.

FIG. 3 demonstrates an example of a system 100 that can be utilized for performing electrical mapping of electrical activity. The system 100 can also be employed to determine a sensing zone for a selected ROI or to identify an anatomical region based on a selected sensing zone. For instance, the system 100 can perform the assessment of a patient's heart 102 in real time as part of a diagnostic or treatment procedure. Alternatively, the system 100 can operate offline based on stored data.

The system 100 can include a measurement system 104 to acquire electrophysiology information for the patient 106. In the example of FIG. 3, a sensor array 108 includes one or more electrodes that can be utilized for recording patient electrical activity. As one example, the sensor array 108 can correspond to an arrangement of body surface electrodes that are distributed over and around the patient's torso for measuring electrical activity associated with the patient's heart (e.g., as part of an ECM procedure). An example of a non-invasive sensor array that can be used is shown and described in International application No. PCT/US20091063803, which was filed 10 Nov. 2009, and is incorporated herein by reference. This non-invasive sensor array corresponds to one example of a full complement of sensors that can include one or more sensing zones. As another example, the sensor array 108 can include an application-specific arrangement of electrodes corresponding to a single sensing zone or multiple discrete sensing zones. The application-specific arrangement of electrodes can be a proper subset of electrodes selected from the full complement of electrodes, such as disclosed herein. Additionally, invasive sensors (not shown) can be used in conjunction with the body surface sensor array 108.

The measurement system 104 receives sensed electrical signals from the corresponding sensor array 108. The measurement system 104 can include appropriate controls and signal processing circuitry for providing corresponding electrical measurement data 110 that describes electrical activity detected by the sensors in the sensor array 108. The measurement data 110 can be stored in memory as analog or digital information. Appropriate time stamps can be utilized for indexing the temporal relationship between the respective measurement data 110 to facilitate the evaluation and analysis thereof. For instance, each of the sensors in the sensor array 108 can simultaneously sense body surface electrical activity and provide corresponding measurement data 110 for a user selected time interval.

An output system 112 is configured to process the electrical measurement data, including for one or more sensing zones on the patient's body 106, and to generate an output 114. The output system 112 can be implemented as machine-readable instructions that, when executed by a processor, perform the methods and functions disclosed herein. The output 114 can present information for one or more ROIs based on the electrical measurement data 110. The output 14 can be stored in memory and provided to a display 116 or other type of output device. As disclosed herein, the type of output 114 and information presented can vary depending on, for example, application requirements of the user.

As an example, the output system 112 can include a map generator 118 that is programmed to generate map data 120 representing a graphical map of electrical activity for one or more ROI based on the electrical measurement data 110 for one or more respective zone. As disclosed herein, the graphical map can represent body surface electrical activity that provides a surrogate estimate for one or more ROI, reconstructed electrical activity for a cardiac envelope (e.g., an epicardial surface), or other electrical characteristics computed therefrom and visualized as a corresponding map. The map generator 118 can generate the map data 120 to visualize such map spatially superimposed on the ROI of a graphical representation of the heart.

In some examples, the output system 112 includes a reconstruction component 122 that reconstructs heart electrical activity by combining the measurement data 110 with geometry data 116 through an inverse algorithm to reconstruct the electrical activity onto a cardiac envelope, such as an epicardial surface or other envelope. Examples of inverse algorithms are disclosed in U.S. Pat. Nos. 7,983,743 and 6,772,004, each of which is incorporated herein by reference. The reconstruction component 122 for example computes coefficients for the transfer matrix $A^{-1}$ to determine heart electrical activity based on the body surface electrical activity represented by the electrical measurement data 110.

The map generator 118 can employ the reconstructed electrical data computed via the inverse method to produce corresponding map data 120 based on reconstructed heart electrical activity computed by the reconstruction component 114 for each ROI. The map data 120 can represent electrical activity of the heart 102, such as corresponding to a plurality of reconstructed electrograms distributed over each ROI for which the sensing zone(s) measured the body surface electrical activity. Alternatively or additionally, an analysis system 124 can compute other electrical characteristics from the reconstructed electrograms, such as disclosed herein. The map generator 118 can in turn produce graphical maps of such electrical characteristics for each ROI.

As a further example, the geometry data 116 may be in the form of graphical representation of the patient's torso, such as image data acquired for the patient 106. Such image processing can include extraction and segmentation of anatomical features, including one or more organs and other structures, from a digital image set. Additionally, a location for each of the electrodes in the sensor array 108 can be included in the geometry data 116, such as by acquiring the image while the electrodes are disposed on the patient and identifying the electrode locations in a coordinate system through appropriate extraction and segmentation. The resulting segmented image data can be converted into a two-dimensional or three-dimensional graphical representation that includes the volume of interest for the patient.

By way of further example, the patient geometry data 172 can be acquired using nearly any imaging modality (e.g., x-ray, computed tomography, magnetic resonance imaging, ultrasound or the like) based on which a corresponding representation can be constructed, such as described herein. Such imaging may be performed concurrently with recording the electrical activity that is utilized to generate the measurement data 110 or the imaging can be performed separately (e.g., before the measurement data has been acquired).

As another example, the geometry data 116 can correspond to a mathematical model of a torso that has been constructed based on image data for the patient's organ. A generic model can also be utilized to provide the geometry data 116. The generic model further may be customized (e.g., deformed) for a given patient, such as based on patient characteristics include size image data, health conditions or the like. Appropriate anatomical or other landmarks, including locations for the electrodes in the sensor array 108 can be represented in the geometry data 116 to facilitate registration of the electrical measurement data 110 and performing the inverse method thereon via the reconstruction component 114. The identification of such landmarks can be done manually (e.g., by a person via image editing software) or automatically (e.g., via image processing techniques). Where the electrical measurement data 110 is for a given sensing zone that can provide surrogate electrical activity for a corresponding ROI of the heart, the geometry data and the transformation matrix utilized for reconstructing electrical signals on the heart can likewise be application-specific to facilitate computations.

In other examples, the map generator 118 can employ BSM/surrogate code 126 for generating the map data 120 directly based on the non-invasive body surface electrical activity (e.g., corresponding to the measurement data 110) without involving reconstruction by solving the inverse solution. In this example, the map data 120 provides a surrogate estimate of cardiac electrical activity for one or more ROI. For instance, the surrogate map data 120 can include measured electric potentials for a given sensing zone to provide a surrogate potential map for the respective ROI associated with such zone. Alternatively, BSM/surrogate code 126 can employ the analysis methods 124 to compute other electrical characteristics for the sensing zone directly from the measured data 110 without solving the inverse problem for reconstructing the signals on the respective ROI. The type of analysis 124 applied to the electrical measurement data 110, if any, for generating the surrogate estimate data can be selected in response to a user input.

The map generator 118 can thus generate the map data 120 based on the surrogate estimate data without the complex computations associated with solving the inverse problem. The map data 120 for the surrogate estimate (e.g., electrical potentials or other characteristics computed for the zone) can include a map that shows variations across the sensing zone. In other examples, the electrical information for a given sensing zone can be aggregated spatially, temporally or both spatially and temporally, for the given zone to produce a value or range of values for a given ROI of the heart. As a further example, surrogate estimates of electrical characteristics can be determined for a plurality of different sensing zones, which can be used by the map generator 118 to generate map data for each respective ROI of the heart. The map generator can generate and update maps to provide a visualization of the surrogate estimates in substantially real time, such as to facilitate providing real-time intraoperative guidance during a procedure, such as disclosed herein.

As another example, an ROI selector 128 can be employed to select an ROI in response to a user input. The ROI can be selected as one of a plurality of predetermined anatomical regions. Alternatively, or additionally, the ROI can be traced on a graphical user interface of the anatomy containing the ROI, such as in response to a user input (e.g., via a mouse, touchscreen). The selected ROI can be utilized for determining a corresponding sensing zone.

In some examples, a sensing zone function 130 can compute the sensing zone for the selected ROI based on the map data 120. For example, the sensing zone function 128 can determine the sensing zone for a given ROI based on a comparison of map data computed for a plurality of different subsets of electrical measurement data relative to map data computed for a full set measurement data (e.g., using a fully compliment of electrodes around the ROI. The comparison can employ from statistical analysis to ascertain a minimized sensing zone that is closest match to the map data. The comparison of map data can be performed automatically by the sensing zone function 130 and/or manual review of respective maps can be performed via the display to select a suitable sensing zone.

In other examples, the ROI selector 128 can be programmed to identify an ROI based on a given sensing zone that has been determined by the zone function 130. For example, the map generator 118 can provide a graphical map for the identified ROI superimposed on a graphical representation of a heart. As disclosed herein (see, e.g., FIG. 9) the ROI can correspond to an anatomical region that is expected to be adversely affected by measurements in a given sensing zone of the patient's body surface (e.g., corresponding to bad channels). This analysis can be performed in situations when the full complement of body surface electrodes is being used as well as in situations when an application-specific arrangement of electrodes is being used. The guidance provided by the map thus can afford a user the opportunity understand how the measurements in the zone may affect resulting analysis. As a result, a user can have an opportunity to correct the problem (e.g., a set of bad channels), if appropriate, or proceed knowing how subsequent analysis of the selected ROI may be affected.

In view of the foregoing, an application-specific arrangement of electrodes can be designed and/or produced to measure given electrical activity of a given respective sensing zone. Such application-specific arrangement of electrodes can be configured to include a spatial distribution of electrodes that reside only within the computed sensing zone. Such an application specific arrangement of electrodes can be implemented, for example, in the form of patches (e.g., single or multiple pieces). For example, a patch for CRT can be configured to allowing for left arm access for a pectoral pocket. The right side can remain free (uncovered) if it does not include a corresponding sensing zone design and if a right pocket is desired. The sensing zone can be thus used for application specific vest designs. Additionally or alternatively, the sensing zone can be used to evaluate the impact of not having sensors in sensing zones, including in real time, such as during a procedure.

As another example, the application specific arrangement of electrodes can be implemented as a complete or partial band that can cover and wrap around a portion of the patient's chest that includes one or more sensing zone. Such band can include one or more clusters of electrodes or arrays distributed along one or more predetermined sensing zones. In other examples, small patches of electrode clusters can be configured for placement in application-specific sensing zones. One or more such patches could be used for acquiring body surface electrical data.

The particular configuration and size of a given application-specific arrangement of electrodes, including patches, bands or the like, can vary depending on the geometry and location of the sensing zone that is determined for each respective application. Additionally, some application-specific arrangements of electrodes can be configured for multiple sensing zones. Placement of the patches can be guided based on manual measurements of the patient's anatomy. Additionally, imaging, which can be performed previously or during a procedure, may further be utilized to guide placement of the electrodes. For example, contributions of individual electrodes can be determined (e.g., by the measurement system 104 and/or the output system 112) with respect to points along one or more ROIs to provide additional feedback to the user for adjusting the position of the application-specific arrangement of electrodes.

Alternatively, a more extensive arrangement of electrodes up to covering the full torso can be utilized and the measurement system 104 and/or the output system 112 can remove measurement data from channels that is outside the zone. That is, the application-specific arrangement of electrodes for a given sensing zone can be implemented by constructing a physical arrangement of electrodes for the zone and/or by configuring the system to process a proper subset of channels corresponding to the zone. In either case, the computational complexity of signal processing and map generation can be reduced relative to traditional systems that process the entire compliment of channels. The application-specific application zone of channels can not only facilitate resulting analysis of electrical activity for the ROI, but do so while maintaining a high degree of accuracy for many applications and procedures (e.g., CRT).

As mentioned above, due to the reduced computational complexity afforded by an application-specific zone, the system 100 can be utilized intraprocedurally for real-time analysis. For instance, the system can be used before, during and after providing a therapy or while programming a therapy delivery system to achieve a desired therapeutic effect.

By way of example, a therapy system 132 can be configured to apply a therapy to the heart via a delivery device 134. In some examples, the therapy device 134 can be an electrically conductive structure, such as an electrode or antenna for providing electrical or radiofrequency therapy. Alternatively, the device 134 can be configured to apply a thermal therapy (e.g., heating or cooling) to the heart 102. The particular type and configuration of the delivery device 134 can depend on the mode of therapy, delivery site and application requirements. The therapy system can include a control 136 configured to control application of therapy, such as in response to a user input. For instance, a trigger (e.g., a switch or button) can be activated by a user to initiate application of therapy. Various therapy parameters can also be set in response to the user input to control the therapy. For the example of electrical stimulation (e.g., for CRT), the parameters can include amplitude, cycle time or the like and further will vary depending on the type of therapy.

In the following example, a therapy delivery device (e.g., an electrode 134) can be positioned in or on a patient's heart 102, such as part of a minimally invasive catheter procedure. As disclosed herein, the sensor array 108 is configured for measuring activity for at least a predetermined sensing zone or a plurality of different sensing zones. Prior to delivering a therapy, which may be before or after the device 134 has been positioned in the patient's body 106, one or more measurements (over respective time intervals) of body surface electrical activity can be made with the sensor array 108. The pre-therapy measurements of electrical activity can be stored as baseline electrical measurement data 110 for each zone over one or more pre-therapy time intervals.

The acquired electrical measurements for each of the plurality of different zones can provide a baseline surrogate estimate of electrical activity (e.g., for each corresponding spatial ROI of the heart. The analysis function 124 can also compute surrogate estimates for electrical characteristics (e.g., activation-repolarization time etc.) for each respective ROI which can also be stored in memory as part of the baseline data for the procedure. In some examples, the analysis function 124 may be programmed to compute the estimate an indication of relative synchrony for a plurality of ROIs based on a comparison of activation and/or depolarization times for each of the ROIs relative to its respective baseline.

After the baseline data has been acquired, therapy can be applied to the heart 102 via the therapy device 132. The measurement system 104 can measure body surface electrical activity from the patient's body during delivery of therapy and/or after the therapy is applied to provide corresponding measurement data. The BSM/surrogate function 126 can provide a surrogate estimate of electrical activity for each of a plurality of corresponding spatial ROIs of the heart based on intra- and/or post-therapy data that was acquired. This can be repeated over a plurality of different available therapy parameters.

As a further example, the system can be utilized to implement a method for targeted analysis of one or more ROIs, including intraprocedurally and in real time. For example, the system 100 can be utilized to calibrate and identify the zones on the body surface that correspond to key anatomical regions. For instance, the anatomical region can include one or more stimulation sites, such as may have been identified as potential responders to CRT. A user can thus employ the electrode 134 and pace at various locations (e.g., in response to a user input to initiate stimulation). The analysis methods 124 of the output system 112 can compute a corresponding earliest activation 'zone' on the body surface in response to the stimulation (e.g., pacing). This can be performed directly on body surface electrical measurement data, for example, without solving the inverse problem and reconstructing the electrical data. In other examples, the analysis 124 can be performed on reconstructed electrical data for the heart. The zone function 130 can in turn identify the input channels on the body surface that provide the earliest activation time, thereby specifying relationship between the zone and the pacing site. As an example, a simple protocol that can be used in current venous lead placement approaches is to pace the potential veins that are amenable to lead placement to determine the relative correspondence to electrical sensors of the array 108, which correspond to a zone on the body surface. This will enable targeted further analysis pertaining to these zones, such as over a range of parameters and pacing protocols. This process can be utilized with other types of lead placement and cardiac therapies.

Figure 4:
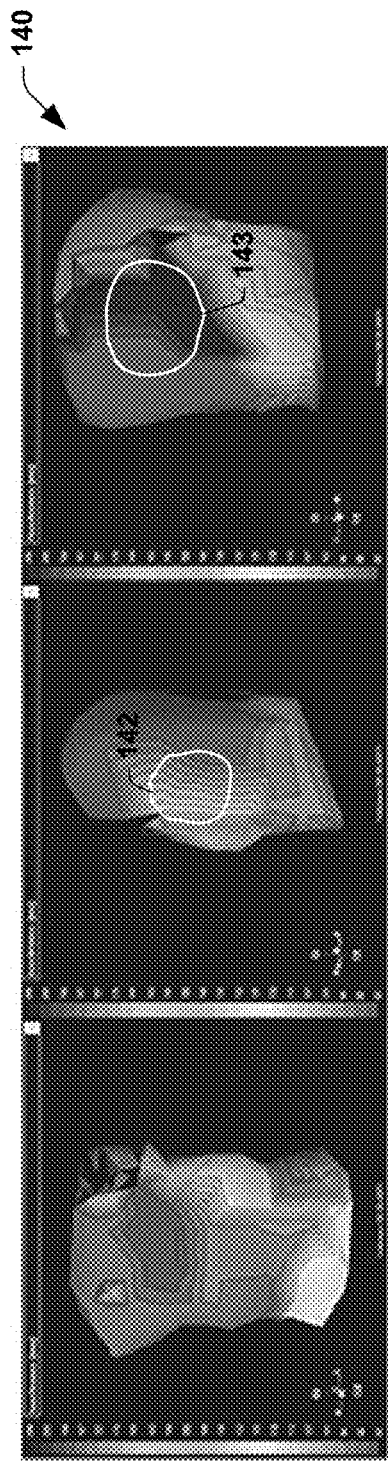
FIG. 4 depicts examples of baseline graphical maps.
Figure 5:
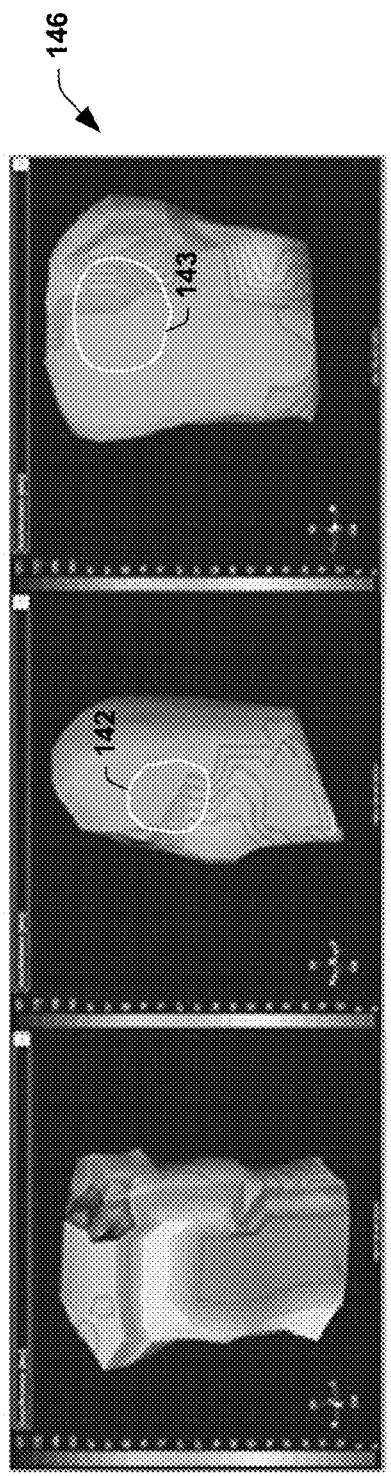
FIG. 5 depicts examples of graphical maps post-therapy.

By way of example, FIGS. 4 and 5 depict graphical maps surrogate electrical activity that can be generated based on the systems and methods disclosed herein, such as part of a CRT procedure. In FIG. 4, baseline body surface activation maps 140 are shown for different ROIs for surrogate regions of the heart, such as based on electrical measurements acquired for a predetermined sensing zone (or zones) before applying a therapy. Also shown in FIG. 4 are different ROIs 142 and 143 for surrogate heart regions, such as can be selected as disclosed herein.

FIG. 5 demonstrates the same types of surrogate maps 146 generated for activation times computed from body surface measurements that have been acquired following delivery of therapy as disclosed herein. For example, the therapy can include electrical or other stimulation, such as part of a CRT procedure. A comparison between the maps depicted FIGS. 4 and 5 demonstrates an improved CRT response for each of the ROIs 142 and 143.

Referring back to FIG. 3, the BSM/surrogate function 126 can further be programmed to compare the pre-therapy baseline surrogate estimate (e.g., of FIG. 4) relative to the post-therapy surrogate estimate of electrical activity (e.g., of FIG. 5). The comparison can be made between the pre-therapy and post-therapy surrogate estimates for the same sensing zone such as to provide an indication of the change in the cardiac electrical activity for a given therapy relative to the baseline measurements. Such comparison can also be performed for electrical characteristics computed by the analysis function 124 based on the pre-therapy baseline results and post therapy measured electrical activity for the given sensing zone. This can further be performed for each of a plurality of different respective sensing zones that provide surrogate estimates for different defined regions of the heart. In addition to comparing the baseline surrogate electrical characteristics relative to the intra- and/or post therapy surrogates, the analysis function 126 can compare the different electrical characteristics for the same ROI or a combination of ROIs for different therapy parameters and protocols. The therapy parameters can be stored with the electrical measurement data that is acquired during or after application of therapy. In this way, a user can review the results to help identify which therapy parameters and protocols help achieve a desired result.

The map generator 118 can also generate a map to depict the pre- and post-therapy surrogate estimates. As disclosed above, the surrogate estimates for each sensing zone can be displayed in graphical maps superimposing the estimated values on the respective anatomic ROIs of the heart. The pre- and post-therapy maps (e.g., shown in FIGS. 4 and 5) can be displayed simultaneously at the display 116 such as in separate windows. Additionally, or alternatively, a comparative map (not shown) can be generated and visualized as a graphical map on the display 116.

As further example, the analysis function 124 can be programmed to calculate pseudo activation times of non-invasively measured body surface electrical activity. For instance, the activation times can be calculated using a dv/dt method or another method (e.g., directional activation, such as disclosed in PCT Application No. PCT/US11/51954). The pseudo activation time can be computed for pre-therapy (e.g., baseline) and post-therapy body surface electrical data. Even without reconstructing the electrical data onto a cardiac envelope via solving the inverse problem, corresponding patterns of the pseudo activation times for one or more zones can be analyzed and visualized as a graphical map to provide a broad global estimate of sequence of activation, conduction velocity, early and late activation or each of a plurality of different sensing zones. Slow or blocked conduction can also be roughly estimated from such line patterns on the body surface as well. This can be used, for example, to delineate the approximately location of the septum or even the engagement of the conduction system.

Continuing with the example of providing therapy to the heart via the device 134, body surface activation maps or potential map patterns for each sensing zone can be generated to provide surrogate estimates of synchrony information that can be utilized to help tune therapy parameters. The synchrony information for a given sensing zone can be derived from measurements made at different time intervals, each having unique different therapy parameters, can be compared to provide an indication how the corresponding ROI responds to the different therapy parameters. The comparison can be made by computing the difference between electrical characteristics in each zone between the baseline data and data acquired for each of the different therapy parameters. Alternatively or additionally, graphical maps can be presented concurrently on the display 116 for comparison by the user.

As an example, the average timing change for the same given zone can be compared over a plurality of different pacing protocols and pacing parameters. The activation times or potential patterns can be compared for the same ROI. Alternatively or additionally, activation times or potential patterns can be compared for a combination of plural ROIs between baseline maps and paced maps including CRT.

In addition to comparing different surrogate estimates derived for the same ROI over different therapy parameters, as mentioned above, the output system 100 can be utilized to facilitate spatial analysis of surrogate estimates of electrical information among a spatially diverse set of sensing zones. Such analysis can help characterize relative timing information for different spatial regions of the heart. For example, the electrical measurement data 110 can include body surface potentials acquired for a plurality of different predetermined sensing zones for a plurality of different time intervals. Each measurement time interval can correspond to a unique combination of therapy protocol and therapy parameters. The BSM/surrogate function 122 thus can compute a surrogate estimate of electrical activity or electrical characteristics based on a comparison of relative timing information computed based on the measured body surface electrical data for a combination of different zones at each measurement interval. By tracking changes in the relative timing (e.g., activation timing, or average timing, synchrony or dyssynchrony) for the different body surface zones with respect to different therapy protocols and parameters, the analysis function 126 can provide an estimate in improvement of cardiac function for the corresponding ROIs of the heart. The map generator 118 can generate graphical maps to demonstrate and visualize (e.g., via graphical map) the improvements to the user. Due to the reduced processing associated with the approach disclosed herein, the visualization can be generated in substantially real time graphical maps that may be update dynamically during testing.

As another example, the direction of the changes in timing can also be employed to estimate improvement or reduction in synchrony or dyssynchrony. The activation times or potential patterns for can be evaluated to estimate cardiac dyssynchrony and classify the patient as 'dyssynchronous' based on threshold values determined from normal body surface maps. The activation times or potential patterns can be compared for the same region or a combination of regions for various combinations of pacing protocols and device parameters. The resulting timing information and direction of changes in timing can be implemented (e.g., as manual or automated feedback to the therapy system 132) to help control selection of the therapy parameters. QRST intervals or other measures of activation-repolarization measures could be also quantified based on surrogate estimates of electrical activity and compared similar to as disclosed above.

In view of the foregoing, the output system 118 can be programmed to provide various temporal and spatial comparisons of surrogate estimates of electrical characteristics derived from electrical activity measured for one or a combination of sensing zones over a plurality of different time intervals. Different time intervals can correspond to different therapy parameters and protocols, such that the comparative data can be analyzed to determine which combination of parameters will achieve a desired therapeutic effect as disclosed herein. While the examples disclosed above in relation to programming therapy delivery were described in the context of using surrogate estimates (in the absence of solving the inverse problem), the same methods can be implemented on reconstructed electrograms for one or more sensing zone over a range of therapy parameters and protocols.

As an example, another method to calibrate and identify the spatial zones on the body surface that correspond to key anatomical regions (e.g., pertaining to CRT) is to pace at various known locations and note the corresponding earliest activation 'zone' on the body surface. The activation time for each of the body surface electrodes can be computed, and the set of electrodes determined having the earliest activation time in response to the pacing stimulus can define a corresponding sensing zone for the stimulated anatomical region. For instance, a percentage of those electrodes exhibiting the earliest activation time can be defined as a respective sensing zone for the stimulated region. An example of a simple protocol that can be used in current venous lead placement approaches is to pace the potential veins that are amenable to lead placement to determine the relative correspondence on the body surface. This will enable targeted analysis pertaining to these zones.

Further accuracy and refinement can be obtained by applying known anatomical constraints obtained from simple chest x-ray or fluoroscopic imaging to estimate the approximate location of the heart. Such anatomical location constraints can include, for example, center of the heart, apex of the heart, anterior septum (LAD), posterior septum (PDA), outflow tracts, valves and the like.

Figure 6:
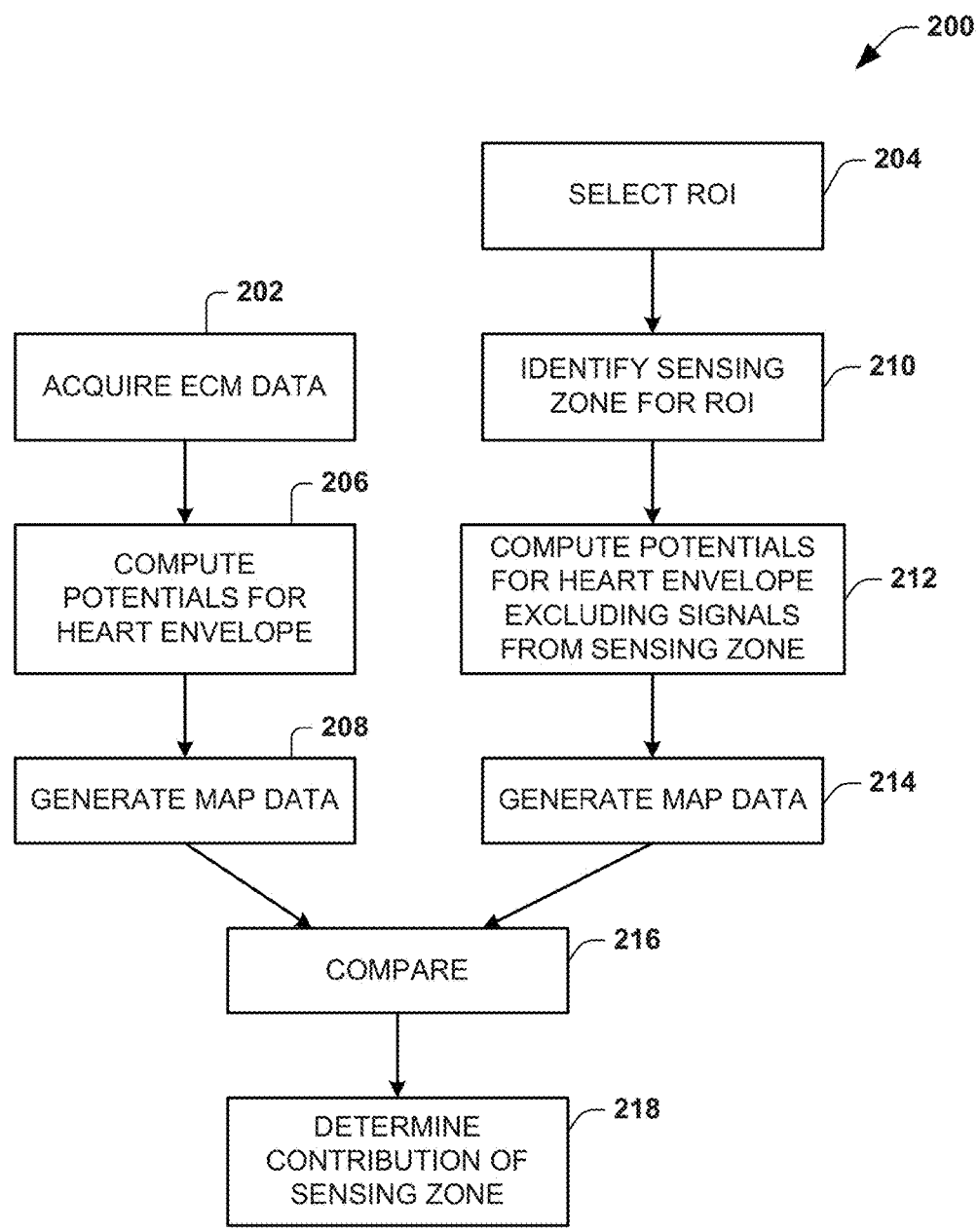
FIG. 6 depicts an example of a workflow to be utilized to determine a sensing zone.

FIG. 6 demonstrates an example of a workflow 200 that can be utilized for evaluating contributions of a selected region of interest for a patient's heart. In the workflow, at 202 ECM data is acquired. The ECM data can include body surface electrical data as well as geometry data such as can be acquired via a corresponding imaging modality. Alternatively, the geometry data can correspond to a model of a patient's heart. The model can be a generic model, a generic model adjusted based on some patient specific data or a model derived from patient-specific imaging data. For instance, a generic model can be adjusted based on manual measurements of the patient (e.g., chest measurements, patient weight or the like), based on measurements from imaging (e.g., x-ray, fluoroscopy, and ultrasound) or a combination of patient information.

In the example workflow of FIG. 6, at 204, a region of interest of a patient's heart is also selected. The region of interest can correspond to any region of a patient's heart for which it is desirable to understand the contribution of a corresponding sensing zone to ECM analysis. In the example of FIG. 6 there are two generally parallel paths that are utilized for comparing and evaluating the effect of excluding electrode locations (and corresponding electrode signals) that do not significantly affect the accurate calculation of maps. Parallel does not require concurrent operations but instead indicates that the paths are sufficiently separate as to generate map data for different subsets taken from a common set of electrical measurements. In the following example, one subset is a proper subset of the other.

With the acquired ECM data, at 206 potentials for a heart envelope can be computed. As used herein, the heart envelope can refer to any surface (e.g., actual or virtual) that may reside on, inside or outside a patient's heart that is spaced radially inwardly from the body surface at which the ECM data is acquired (at 202). In one example, the heart envelope can correspond to the outer three-dimensional surface of the epicardium, which may be the actual outer surface or an approximation thereof. At 208, corresponding map data can be generated based on the computed potentials for the heart envelope.

In the other processing path, at 210, a sensing zone at the body surface for the selected ROI is identified, such as disclosed herein. At 212, the potentials for a heart envelope can be computed based on measurement data excluding the signals from sensors residing in the sensing zone that has been identified (at 210) for the ROI. At 214, corresponding map data can be generated from the heart electrical activity computed at 212.

At 216, the respective maps (generated at 208 and 214) can be compared. The comparison can be made via one or more statistical methods. At 218, the contribution of the sensing zone for the ROI can be determined based on the comparison. For example, if there is a significant difference in the resulting maps, then the impact of removing the sensing zone for the selected region of interest is significant, which can be quantified by the statistical methods. On the other hand, if the comparison indicates that the maps are sufficiently similar, then the identified sensing zone for the ROI can be removed from the analysis while retaining sufficient accuracy in the resulting ECM data. Analysis similar to FIG. 6 can be repeatedly performed as part of the analysis for determining a configuration an arrangement of electrodes for a variety of specially adapted purposes.

Figure 7:
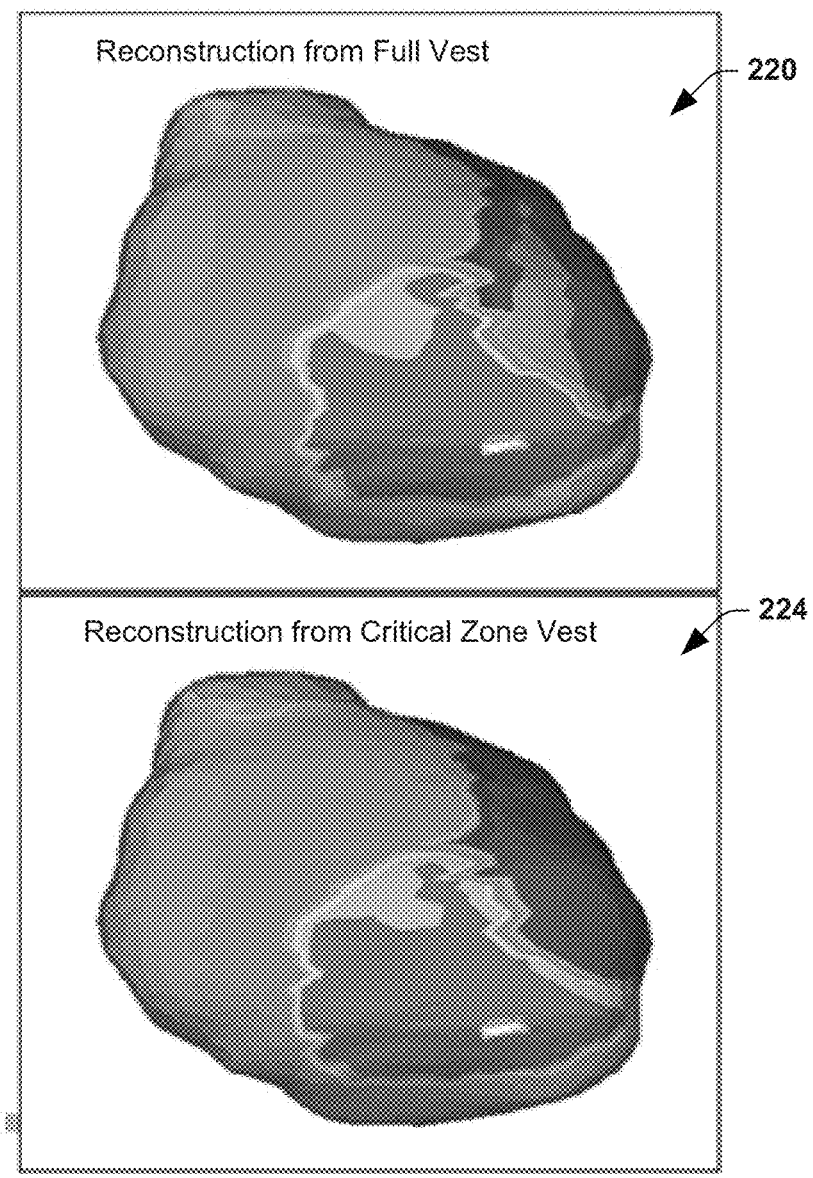
FIG. 7 depicts a comparative example of reconstructed heart electrical activity.

By way of example, FIG. 7 demonstrates a comparative example of reconstructed heart electrical activity for a heart envelope (e.g., the epicardial surface). In this example, a graphical map 220 for one reconstruction demonstrates results from using a full arrangement of electrodes (e.g., a full vest). For example, the full vest includes an arrangement of electrodes completely surrounding a patient's torso in a generally evenly distributed manner. In some examples, there can be greater than about 200 electrodes in the form of a vest.

Another representation of reconstructed heart electrical activity, demonstrated at 224, corresponds to ECM data computed for an application-specific arrangement of electrodes (e.g., a reduced number of electrodes). That is the graphical map 224 can be generated (e.g., by the reconstruction method 120) based on electrical measurement data provided from an arrangement of electrodes configured for a predetermined sensing zone based upon the methods disclosed herein. The sensing zone in this example includes the reduced number of electrodes, distributed mainly across front, left and back locations of the patient's body.

A visual inspection of the reconstructed ECM for the full vest, demonstrated at 220, and the reconstruction 224 for the application-specific arrangement of electrodes demonstrates very similar results. The arrangement of electrodes for the application-specific arrangement of electrodes corresponds to a much simpler vest having a proper subset of electrodes from the full vest corresponding to a determined sensing zone for a selected ROI. In the example of FIG. 7, for example, the application-specific arrangement of electrodes can correspond to a vest having an ROI configured for performing CRT.

Figure 8:
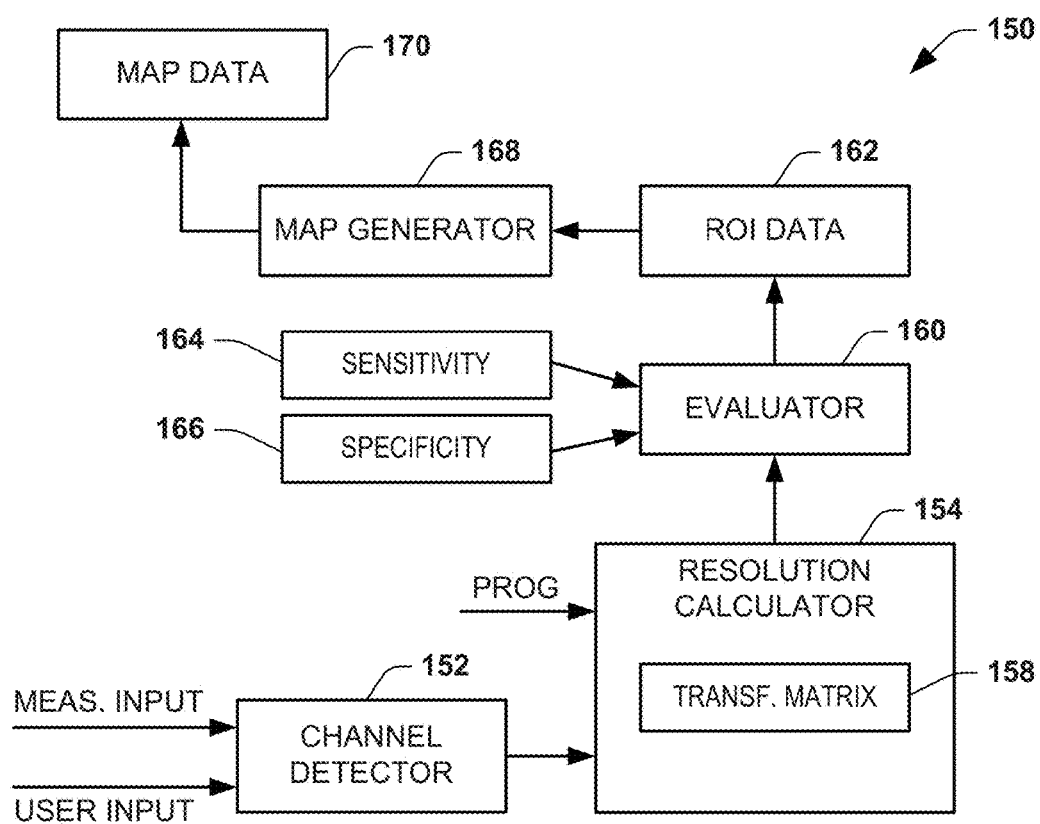
FIG. 8 depicts an example of a resolution calculation system.

FIG. 8 demonstrates an example of a system 150 for indicating one or more ROIs affected by contributions of electrodes residing within a given sensing zone. In some examples, the sensing zone can correspond to locations on the body surface where one or more bad channels reside or locations that can be otherwise identified, such as in response to a user input.

In the example of FIG. 8, a channel detector 152 is configured to identify a subset of channels, corresponding to one or more sensing zones expected to adversely affect mapping of body surface electrical activity acquired for the zone. The channel detector 152 can identify the zone in response to a user input, based on measurement data (e.g., electrical measurement data 110 of FIG. 3) or a combination thereof. In some examples, the channel detector 154 can designate the sensing zone as including a set of bad channels. A bad channel can correspond to a body surface location at which an electrode does not adequately contact the body surface, which may be intentional or unintentional. Additionally or alternatively, a bad channel can correspond to channel having a signal to noise ratio that is below a threshold.

A resolution calculator 154 is configured to compute an indication of the contribution that each electrode in the identified sensing zone (channels provided by the channel detector 152) has on the inverse solution for each point on the heart. The contribution, for example, can be determined by the resolution calculator computing coefficients for the transformation matrix 158 for each of the sensing channels for the zone for each point on the cardiac envelope.

An evaluator 160 can analyze the computed coefficients (e.g., an absolute value thereof) to generate ROI data 162. For example, the evaluator 160 can employ a specificity parameter 164 and a sensitivity parameter 166 to control how the ROI 162 is determined. The sensitivity parameter 166 can be a user programmable threshold that can be set and compared to the absolute value of the computed transformation matrix coefficients. If a coefficient exceeds the threshold for a given node on the cardiac envelope, the electrode can be identified for the node as having a sufficient contribution to the reconstructed data at such node. There can be one or more coefficients at a given point on the envelope that can exceed the threshold. For instance, increasing the threshold value increases the spatial sensitivity for identifying a low resolution region on the cardiac envelope as it requires a greater spatial contribution. The sensitivity parameter can set a minimum number of hits for the computed coefficients needed to designate a low resolution area. Increasing the number of hits can increase the overall specificity for precisely identifying a low resolution area. Thus by setting the specificity and sensitivity parameters appropriately for a given sensing system, one or more low resolution region on the heart can be determined and used to inform the user accordingly.

In some examples, the specificity and sensitivity parameters 164 and 166 can be pre-programmed (e.g., to default values) for system 150 (as well as the system 100 of FIG. 3) to determine circumstances when bad channels on the vest tend to create artifacts in the reconstruction. The information can be presented to the user as a notice or warning, such as afford an opportunity to take corrective action, such as by adjusting the electrodes to improve the sensing ability or changing the contribution of electrodes to the ROI. After corrective action is taken, the system 150 can recompute coefficients, such as in response to a user input, to determine if one or more low resolution region still exists. In some examples, a user can opt not to take corrective action, such as where the low resolution region is outside of a ROI considered important to the user for a given analysis. Alternatively or additionally, a user can adjust one or more of the sensitivity or specificity parameters to reevaluate the impact of the identified sensing zone (e.g., bad channels) on the inverse solution. Additional analysis by the evaluator may include comparing a computed low resolution region with respect to a user-selected ROI, such that an overlap between such regions can result in generating a warning or other notification.

A map generator 168 can provide map data 170 for rendering a visualization based on the ROI data 162. For instance, the map data can be utilized for providing a graphical map of a low resolution region that is superimposed on a graphical map of a heart. The map generator 168 can correspond to the map generator 118 of FIG. 3, and the graphical map can be a three-dimensional map.

Figure 9:
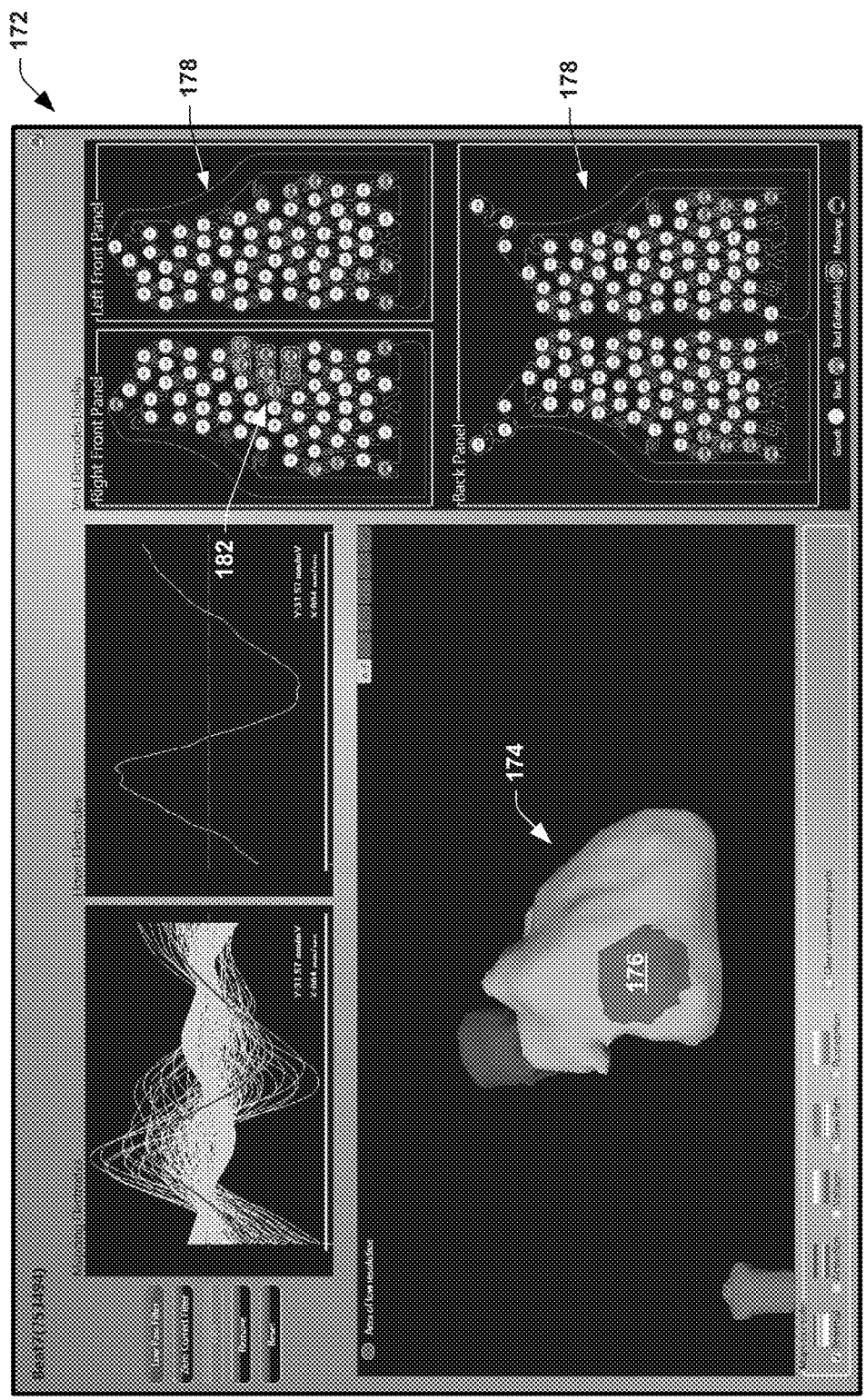
FIG. 9 depicts an example of a graphical user interface that can be utilized in conjunction with the system of FIG. 8.

FIG. 9 depicts an example of a graphical user interface (GUI) 172 that can be utilized for accessing the functions and methods of the system 150 demonstrated in FIG. 8. The GUI 172 can include multiple windows for displaying graphical representations of relevant data, such as can be associated with non-invasive measurement of body surface electrical activity. The GUI 172 also provides an interactive visualization that can be utilized for demonstrating one or more low resolution regions. For example the GUI 172 can include a graphical map 174 of a low resolution region 176 superimposed on a heart. The low resolution region can be computed according to the method of FIG. 8. The GUI can also include an interactive graphical display 178 of each of an arrangement of electrodes, demonstrated as including right and left front panels and a back panel. Other numbers and arrangements of electrodes can also be utilized, including the application specific electrode arrangements disclosed herein.

The electrode display 178 can provide relevant status information of electrodes. For instance the electrode display can identify bad channels by graphically or otherwise differentiating the bad channels from other electrode channels. The designation of channels can be described by a scale 180, such as designating channels as good, bad, bad but editable and missing. Signals utilized for mapping the measured body surface potentials to the heart can also be displayed. A user can also manually designate a given channel as bad, which will result in the measurement data for such electrode being omitted from processing while it is designated as a bad channel. In the example of FIG. 9, the group of channels in the right front panel, demonstrated at 182, has been designated as bad channels but editable. In this example, the resulting low resolution region 176 thus identifies the region of the heart that is adversely affected by the bad electrodes 182.

Figure 10:
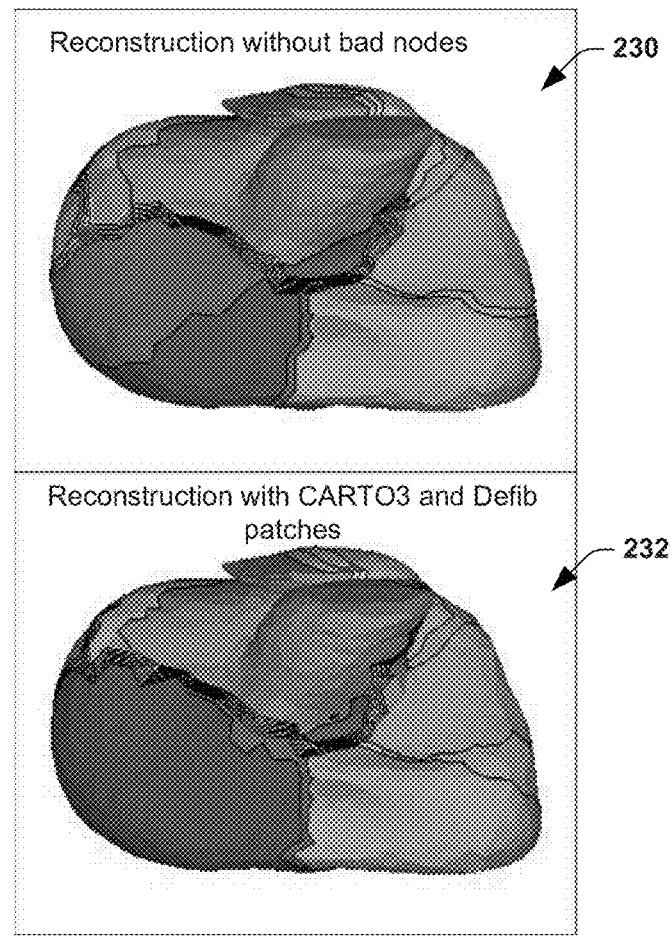
FIG. 10 depicts a simulated example comparison of reconstructed heart electrical activity for a given arrangement of electrodes in a sensing zone with and without bad channels.

As a further example, FIG. 10 demonstrates graphical maps 230 and 232 representing of reconstructed heart electrical activity that has been computed from different sets of non-invasive body surface electrical measurements. In the example of FIG. 10, the graphical map 230 demonstrates reconstructed ECM data in the form of a potential map without any bad nodes (i.e., without compromising electrodes in a corresponding sensing zone). Also demonstrated is another graphical potential map 232 corresponding to reconstruction performed with patches applied to a patient's body surface, but outside of the sensing zone. For example, the patches can include other sensors and/or defibrillation patches that have been attached to the patient's torso. These other patches thus can overlap with and/or replace sensor electrodes from the arrangement of electrodes. A comparison between the different maps demonstrates that the reconstruction is accurate.

Figure 11:
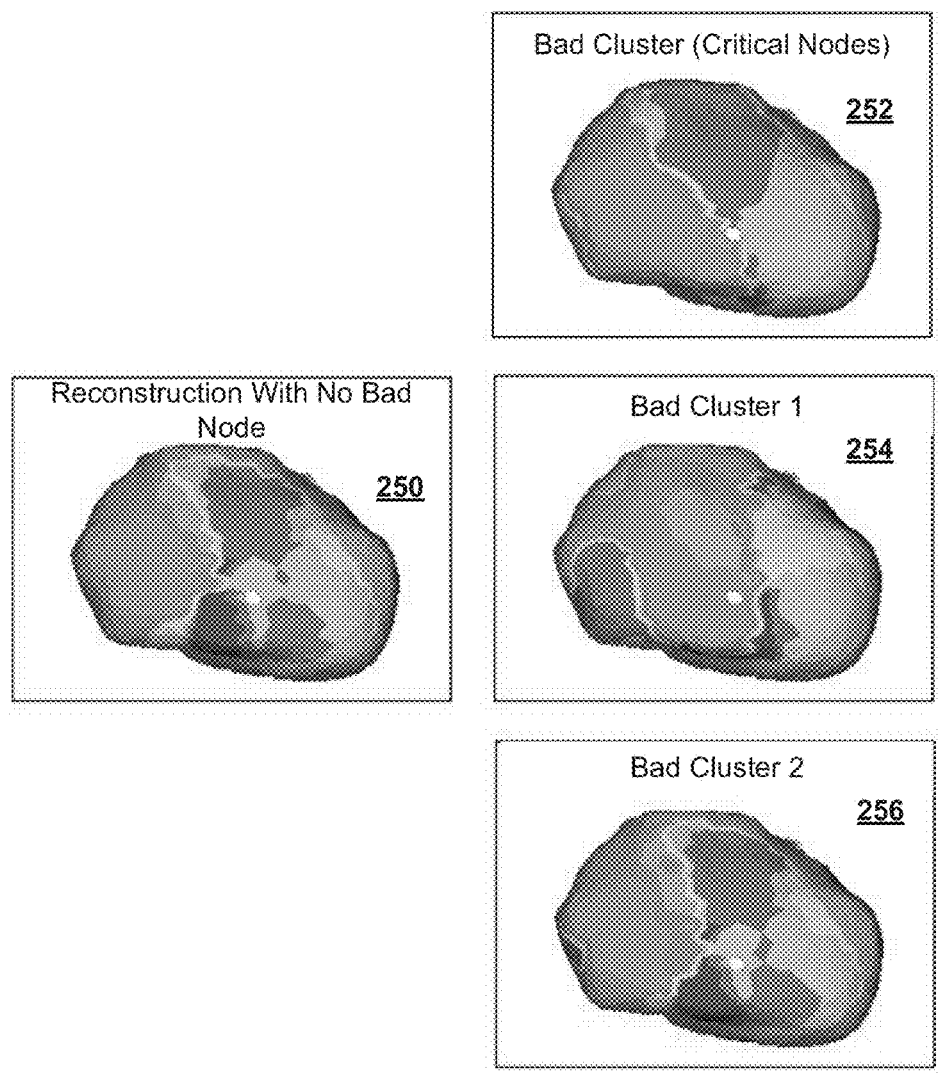
FIG. 11 depicts an example of reconstructed heart electrical activity comparing graphical maps generated from data simulating measurements made with and without bad sensing channels.
Figure 12:
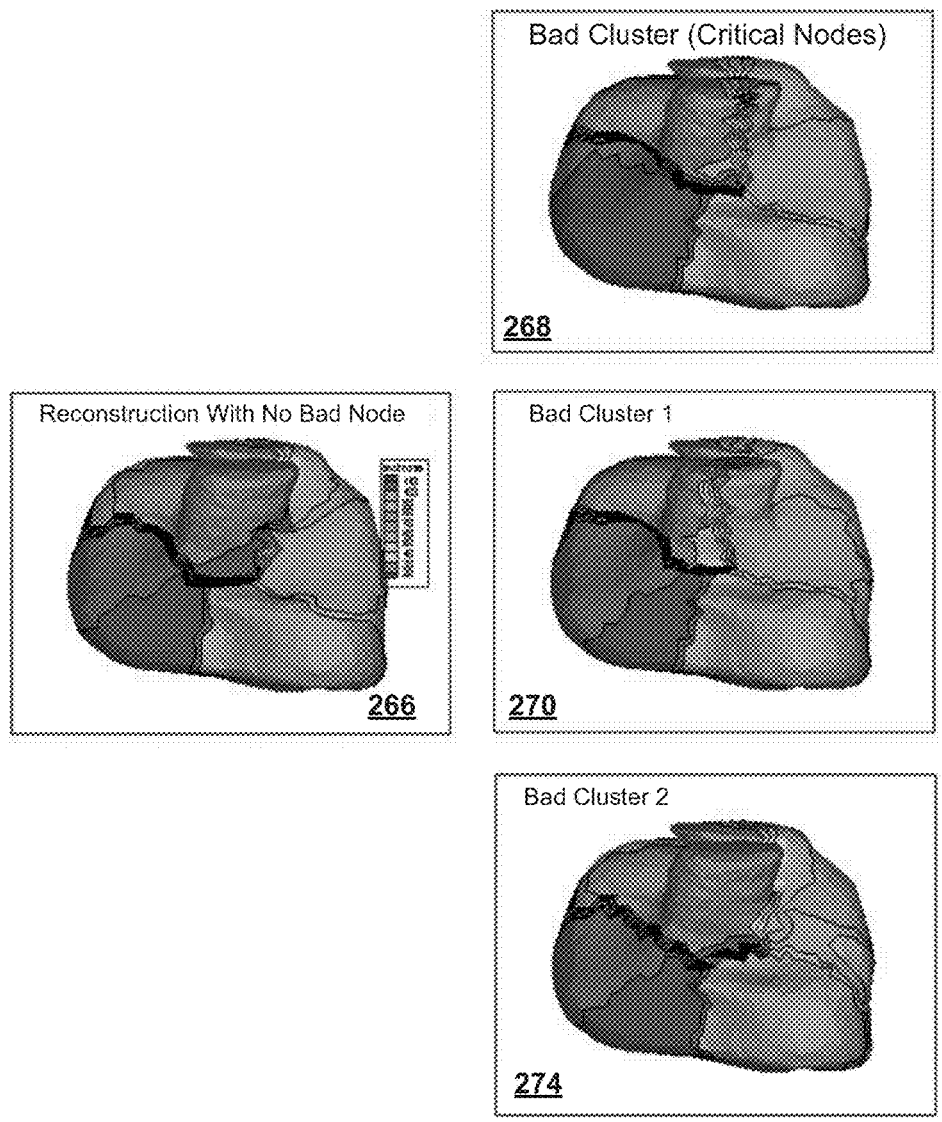
FIG. 12 depicts another example of reconstructed heart electrical activity comparing graphical maps generated from data simulating measurements made with and without bad sensing channels.

By way of further example, FIGS. 11 and 12 demonstrate simulated examples of reconstructed graphical maps for different sensing zones that have been determined for a selected region of interest of a patient's heart. For instance, the maps can be produced via inverse reconstruction for the entire heart surface (or other cardiac envelope) based on electrical measurement and geometry data acquired for all electrodes, as disclosed herein. Each of these examples demonstrates the effect of removing sensed body surface channels, corresponding to electrode sensing locations, demonstrated in these examples as bad channels.

FIG. 11 demonstrates effects of bad channels on a reconstructed potential map for a given sensing zone, such as can be determined for an arrangement of electrodes from a transformation matrix for a given ROI, as disclosed herein. In FIG. 11, four graphical maps are depicted at 250, 252, 254 and 256. Each of the maps 250, 252, 254 and 256 have been generated based on the same electrical measurement data, but with different contributions from certain sensing zones.

For example, the map 250 demonstrates a resulting graphical map where no bad channels exist, such as can be produced via reconstruction for the entire heart surface based on electrical measurement data acquired for all electrodes. The map 252 demonstrates a situation where bad channels form the sensing zone of an arrangement of electrodes that has been determined to be critical (e.g., for sensing electrical activity at a selected ROI). That is, the map 252 is generated in the absence of electrical measurement data from the sensing zone. The map 254 demonstrates a resulting graphical map where a cluster of bad channels 260 (Bad Channel Cluster 1) overlaps with the critical sensing zone. In contrast, the map 256 demonstrates a resulting graphical map where a cluster of bad channels (Bad Channel Cluster 2) resides outside of the critical sensing zone 258. In contrast to the maps 252 and 254, the resulting map 256 is substantially similar to the graphical map 250. This is because the bad channels are outside or mostly outside of the determined sensing zone. That is, different channels are removed from the inputs to the algorithm used to generate the heart electrical activity from the body surface electrical measurements. Thus, the results in the examples of FIG. 11 demonstrate a distinct difference between removing electrodes from inside or outside of the sensing zone.

The example, of FIG. 12 is similar to FIG. 11, in that it demonstrates the effects of removing channels (e.g., bad channels) relative to a given sensing zone, such as can be determined for an arrangement of electrodes from a transformation matrix for a selected ROI, as disclosed herein. In contrast to the example of FIG. 11, however, the sensing zone for the selected ROI is generally evenly distributed across the arrangement of electrodes. In the example of FIG. 12, contribution of corresponding coefficients in the transfer matrix $A^{-1}$ are also evenly distributed across the arrangement of electrode sensing locations.

In the example of FIG. 12, the map 266 demonstrates a resulting graphical map computed based on electrical measurements where no bad channels exist. The map 268 is generated in the absence of electrical measurement data from the sensing zone (e.g., electrical measurement data for the sensing zone are removed). The map 270 demonstrates a resulting graphical map where a cluster of bad channels (Bad Channel Cluster 1) overlaps with the sensing zone. In contrast, the map 274 demonstrates a resulting graphical map where a cluster of bad channels (Bad Channel Cluster 2) resides outside of the critical sensing zone.

A comparison of the graphical maps 266, 268, 270 and 274 demonstrates that the resulting difference between the "gold standard" graphical map 266 for the graphical representation of reconstructed electrical activity for the full set of electrodes relative to the other examples in which electrode clusters have been removed from the analysis are relatively small. This suggests that the impact of removing electrodes for certain ROIs may have little impact on the resulting computations for heart electrical activity data.

Figure 13A:
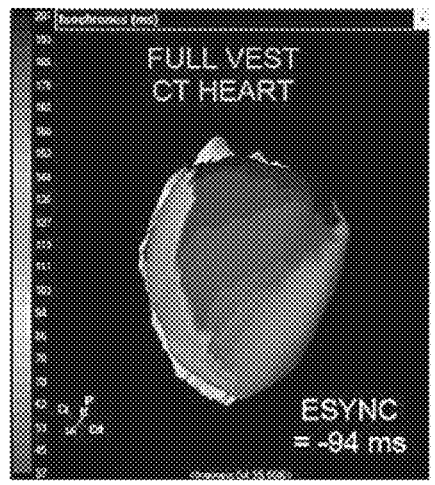
FIGS. 13A, 13B and 13C demonstrate examples of different types of maps that can be generated.
Figure 13B:
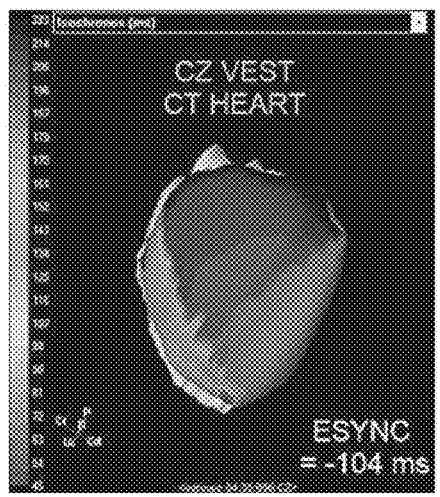
Figure 13C:
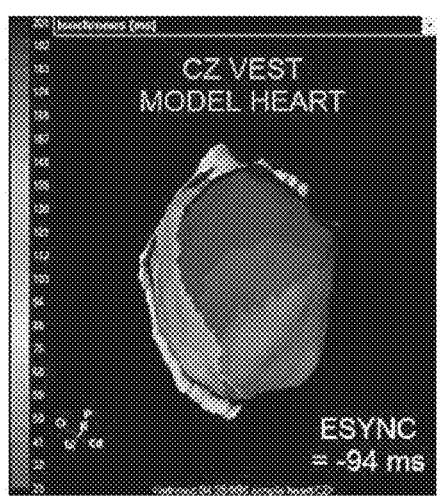

FIGS. 13A, 13B and 13C demonstrate examples of different types of maps that can be generated from a common set of electrical measurement data, such as can be generated by the map generator 118 of FIG. 3. FIG. 13A shows a resulting isochrone map of voltage potentials reconstructed (by solving the inverse problem) onto the surface of a heart based on body surface electrical measurements and patient geometry data (e.g., from a computed tomography scan). FIG. 13B depicts a simulated graphical map of isochrones that is reconstructed generated based on electrical body surface electrical measurements for a predetermined sensing zone and patient geometry data. For instance, the body surface measurements can be obtained using an application-specific arrangement of electrodes determined for a desired ROI, as disclosed herein. FIG. 13C depicts a simulated graphical map of isochrones that is projected onto the heart (in the absence of solving the inverse problem) based on electrical body surface electrical measurements for a predetermined sensing zone and patient geometry data. A comparison of the resulting maps of FIGS. 13A, 13B and 13C demonstrates the efficacy of using an application-specific arrangement of electrodes, without or without inverse reconstruction.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 14. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 14:
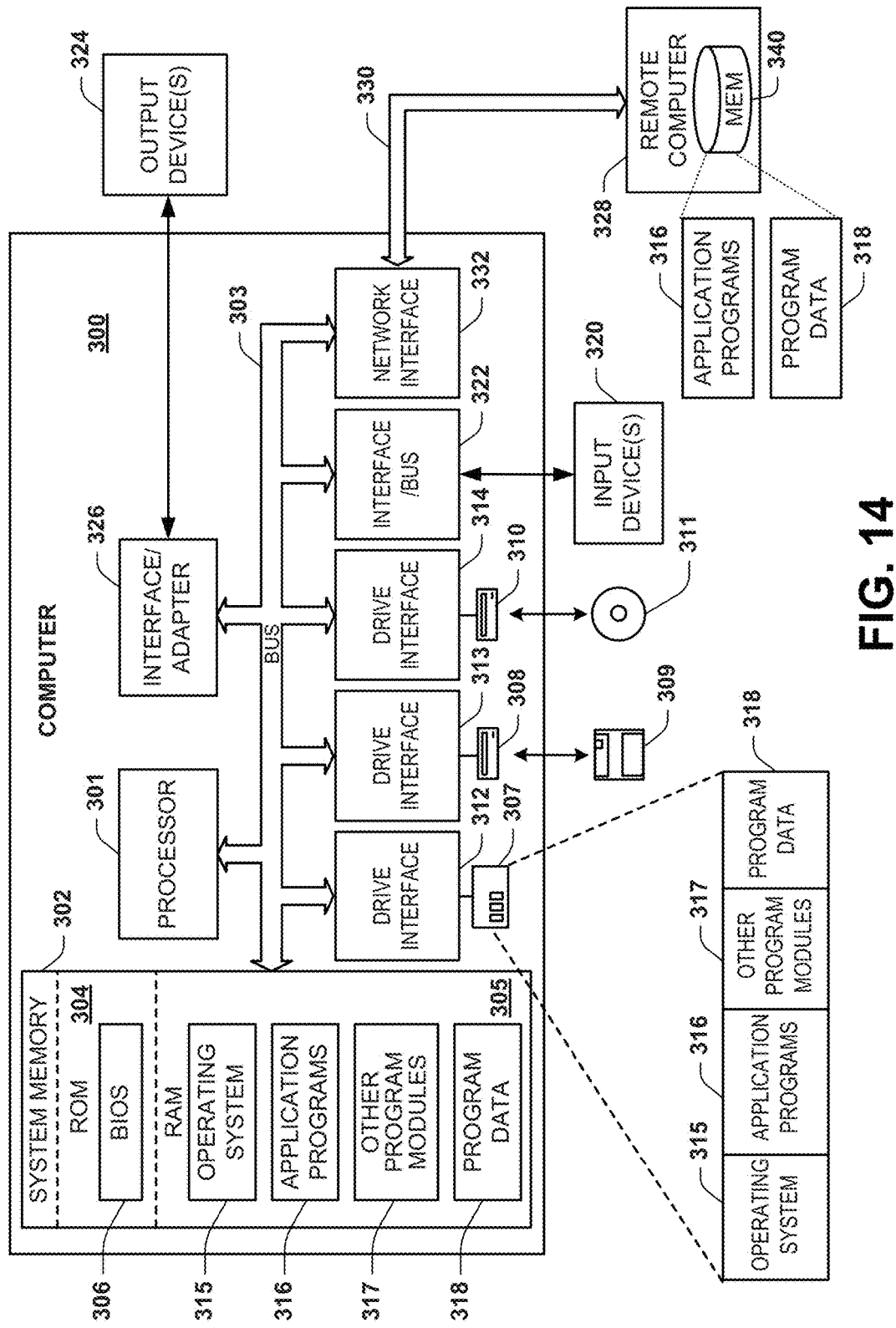
FIG. 14 depicts an example of a computing environment in which the systems and methods disclosed herein can be implemented.

In this regard, FIG. 14 illustrates one example of a computer system 300 that can be employed to execute one or more embodiments of the invention, such as including acquisition and processing of sensor data, processing of image data, as well as analysis of transformed sensor data and image data associated with the analysis of cardiac electrical activity. Computer system 300 can be implemented on one or more general purpose networked computer systems, embedded computer systems, routers, switches, server devices, client devices, various intermediate devices/ nodes or stand alone computer systems. Additionally, computer system 300 can be implemented on various mobile clients such as, for example, a personal digital assistant (PDA), laptop computer, pager, and the like, provided it includes sufficient processing capabilities.

Computer system 300 includes processing unit 301, system memory 302, and system bus 303 that couples various system components, including the system memory, to processing unit 301. Dual microprocessors and other multiprocessor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain machine-readable instructions that can be executed by a processor (e.g., processing unit 301) for implementing one or more functions and methods disclosed herein.

A number of program modules may be stored in drives and RAM 305, including operating system 315, one or more application programs 316, other program modules 317, and program data 318. The application programs and program data can include functions and methods programmed to acquire, process and display electrical data from one or more sensors, such as shown and described herein.

The application programs and program data can include functions and methods programmed to determine a sensing zone as disclosed herein. The application programs and program data can also include functions and methods programmed to generate an electrocardiographic map using a transformation matrix configured to reconstruct electrical signals for a region of interest from a predetermined proper subset of body surface channels for a predetermined sensing zone.

As an example, the application programs 316 and program data 318 can be configured to implement a computer-implemented method that can identify a ROI and determine a zone on a body surface of the patient based on analysis of electrical activity for the ROI relative to electrical activity on the body surface. The resulting electrical activity for the zone on the body surface can provides a surrogate estimate for electrical activity of the region of interest as disclosed herein. In other examples, the electrical activity measured at the body surface can be used to reconstruct electrical activity onto a cardiac envelope, such as a surface of an internal organ (e.g., the heart or brain). The electrical activity, whether it be a surrogate estimate or reconstructed on to the cardiac envelope can be presented in a graphical map via the output device 324). The method can also be stored in a non-transitory machine-readable media 302, 304, 305, 307, 308, 310 and/or 340.

In addition to mapping electrical activity and related computed electrical characteristics, as disclosed herein, the computer system 100 can also be configured store and execute instructions to compute a low resolution region of interest based on a set of designated input channels (e.g., bad channels), as disclosed with respect to FIGS. 8 and 9.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A computer-implemented method comprising:
   identifying a region of interest for an anatomical structure located within a patient's body; and
   defining a spatial zone as a subset of a plurality of electrodes on a body surface of the patient's body corresponding to the region of interest by correlating electrical activity at the region of interest with body surface electric activity measured by the subset of the plurality of electrodes, wherein the body surface electrical activity in the spatial zone provides a surrogate estimate for electrical activity of the region of interest.

2. The method of claim 1, further comprising:
   acquiring electrical signals from the zone or outside the zone; and
   converting the acquired electrical signals to corresponding reconstructed electrical signals for the region of interest via an inverse reconstruction based on an inverse matrix of influence coefficients.

3. The method of claim 2, further comprising generating a graphical map based on the corresponding reconstructed electrical signals for the region of interest.

4. The method of claim 1, wherein the region of interest comprises a selected region of a heart in the patient's body, the method further comprising:
   acquiring body surface electrical potentials from at least the zone; and
   analyzing the acquired body surface electrical potentials for the zone to provide electrical information that is spatially relevant for the selected region of the heart.

5. The method of claim 4, further comprising generating a graphical map for the selected region of the heart based on the acquired body surface electrical potentials to represent the electrical information that is spatially relevant for the selected region of the heart.

6. The method of claim 4, wherein the analyzing further comprises computing an activation time for each of a plurality of points residing in the zone based on the acquired body surface electrical potentials, which correspond to the activation time for each of a plurality of nodes in the region of interest.

7. The method of claim 1, wherein the region of interest comprises a region of a heart in the patient's body, the method further comprising:
   acquiring electrical potentials for each of a plurality of different predetermined zones on the body surface from a plurality of electrodes, wherein the plurality of different predetermined zones each comprises a subset of the plurality of electrodes; and
   analyzing the acquired electrical potentials for each of the plurality of different zones to compute a plurality of surrogate estimates of electrical activity for each of a plurality of corresponding spatial regions of interest of the heart.

8. The method of claim 7, wherein the plurality of surrogate estimates provide an indication of at least one of an activation time or a recovery time for each of the plurality of corresponding spatial regions of the heart.

9. The method of claim 8, further comprising:
   identifying a proper subset of body surface channels that contribute the most to each and every location of the heart; and
   constructing a transformation matrix for the identified proper subset of body surface channels.

10. The method of claim 7, wherein the plurality of surrogate estimates provide an indication of relative synchrony among the plurality of corresponding spatial regions of the heart.

11. The method of claim 7, wherein the acquiring further comprises:
    acquiring a first set of body surface electrical data by measuring electrical potentials for each of the plurality of different predetermined zones on the body surface during a first time interval; and
    acquiring a second set of body surface electrical data by measuring electrical potentials for each of the plurality of different predetermined zones on the body surface during another time interval;
    the method further comprising:
    computing a first surrogate estimate of electrical activity for each of a plurality of corresponding spatial regions of interest of the heart based on the first set of body surface electrical data; and
    computing a second surrogate estimate of electrical activity for each of a plurality of corresponding spatial regions of interest of the heart based on the second set of body surface electrical data.

12. The method of claim 11, further comprising at least one of spatially and temporally comparing the first surrogate estimate of electrical activity and the second surrogate estimate of electrical activity.

13. The method of claim 11, wherein the first time interval is before applying a therapy to a given spatial region of the heart, the another time interval being one of during or after the therapy is applied to the given spatial region of the heart.

14. The method of claim 13, wherein the therapy comprises at least one of an electrical stimulation therapy, a radio frequency therapy and a thermal therapy.

15. The method of claim 11, further comprising generating a graphical map based on the first surrogate estimate of electrical activity and generating another graphical map based on the second surrogate estimate of electrical activity.

16. The method of claim 7, wherein the acquiring further comprises:
    acquiring a first set of body surface electrical data by measuring electrical potentials for at least one of the plurality of different predetermined zones on the body surface during a first time interval; and acquiring a second set of body surface electrical data by measuring electrical potentials for the same at least one of the plurality of different predetermined zones on the body surface during another time interval;
the method further comprising:
computing a first surrogate estimate of electrical activity for each of a plurality of corresponding spatial regions of interest of the heart based on the first set of body surface electrical data; and
computing a second surrogate estimate of electrical activity for each of a plurality of corresponding spatial regions of interest of the heart based on the second set of body surface electrical data.

17. The method of claim 16, further comprising comparing the first surrogate estimate of electrical activity and the second surrogate estimate of electrical activity.

18. The method of claim 16, wherein the first time interval is before applying a therapy to a given spatial region of the heart, the another time interval being one of during or after the therapy is applied to the given spatial region of the heart.

19. The method of claim 18, wherein the therapy comprises at least one of an electrical stimulation therapy, a radio frequency therapy and a thermal therapy.

20. The method of claim 18, further comprising concurrently displaying a graphical map of the first surrogate estimate of electrical activity and the second surrogate estimate of electrical activity.

21. The method of claim 1, further comprising:
accessing electrical data corresponding to electrical signals sensed from body surface electrodes, at least some of which are arranged for sensing electrical activity for the zone; and
generating a graphical map of a heart in the patient's body that includes a representation of electrical information for the region of interest based on the electrical data sensed for the zone.

22. The method of claim 21, wherein multiple instances of the graphical map are generated based on the electrical data acquired at different times during application of a therapy.

23. The method of claim 22, wherein generating the graphical map includes at least one of:
generating the graphical map of the heart based on reconstructed electrical signals computed by solving an inverse problem based on the electrical signals sensed from the body surface electrodes based on an inverse matrix of influence coefficients; and
generating the graphical map of the heart based on reconstructed electrical signals computed by solving the inverse problem based on the surrogate estimate for electrical activity of the region of interest based on the inverse matrix of influence coefficients.

24. The method of claim 1, wherein the region of interest is identified based on the zone.

25. The method of claim 24, further comprising determining a set of one or more sensing channels, corresponding to the zone, expected to adversely affect mapping of body surface electrical activity acquired for the zone,
wherein the region of interest corresponds to a low resolution region of the anatomical structure that is identified based on coefficients of a transformation matrix calculated for each of the sensing channels for the zone.

26. The method of claim 25, further comprising generating a graphical map for the anatomical structure that includes a representation for a location of the low resolution region.

27. The method of claim 25, wherein an impact of the set of sensing channels on a resolution for the region of interest is determined based on at least one of a specificity parameter and a sensitivity parameter.

28. The method of claim 1, wherein the region of interest comprises a plurality of nodes,
further comprising for each node residing within the region of interest, determining a contribution of each of a plurality of body surface electrode locations based on computing coefficients of a transformation matrix for each respective node of the region of interest, and evaluating the contribution of each of the plurality of body surface electrode locations to the plurality of nodes to determine the spatial zone, wherein a proper subset of the plurality of body surface electrodes defines the zone.

29. The method of claim 1, wherein the region of interest comprises a selected region of a heart in the patient's body, the method further comprising:
accessing body surface electrical potentials sensed according to an arrangement of body surface electrodes applied to at least the zone at the body surface of the patient;
analyzing the acquired body surface electrical potentials for the zone to provide electrical information that is spatially relevant for the selected region of the heart; and
generating a graphical map of electrical activity for the selected region of the heart based on the body surface electrical potentials measured for the zone.

30. A non-transitory computer-readable medium having instructions stored thereon, the instructions being executable by a processor to perform a method comprising:
accessing electrical data measured by a selected set of body surface electrodes that define a sensing zone on a surface of a patient's body that is spaced apart from a given region of interest of the patient's heart;
determining a surrogate estimate for electrical activity of the given region of interest based on analysis of the electrical data from the sensing zone and;
defining a spatial zone within the sensing zone whereby the resulting electrical activity within the zone provides a surrogate estimate for the electrical activity of the given region of interest.

31. A non-transitory computer-readable medium having instructions stored thereon, the instructions being executable by a processor to perform a method comprising:
accessing electrical data measured by a selected set of body surface electrodes that define a predetermined sensing zone on a body surface of a patient that is spaced apart from and mapped deterministically to a surrogate estimate for the electrical activity of given region of interest of the patient's heart;
reconstructing electrical activity for the given region of interest of the patient's heart based on geometry data and the electrical data measured by the selected set of body surface electrodes that defines the predetermined sensing zone on the body surface; and
generating a graphical map of electrical activity for the region of interest of the patient's heart based on the reconstructed electrical activity.

32. A non-transitory computer-readable medium having instructions executable by a processor, the instructions comprising:
directing a channel detector to determine a subset of input channels from a plurality of input channels, wherein the subset of input channels is expected to affect mapping of body surface electrical activity within a sensing zone on the body surface, wherein the subset of input channels correspond to a subset of body surface electrodes;

directing a resolution calculator to compute coefficients of a transformation matrix for each channel of the subset of input channels in the sensing zone; and directing an evaluator to identify a low resolution spatial region on a cardiac envelope of a generated electrocardiographic map based on an evaluation of the coefficients, said low resolution spatial region utilized to identify bad channels within the plurality of input channels.

\* \* \* \* \*